United States Patent
Hergenrother et al.

(10) Patent No.: US 11,510,919 B2
(45) Date of Patent: Nov. 29, 2022

(54) CANCER THERAPY BY DEGRADING DUAL MEK SIGNALING

(71) Applicant: The Board of Trustees of the University of Illinois, Urbana, IL (US)

(72) Inventors: Paul J. Hergenrother, Champaign, IL (US); Jessie Peh, Urbana, IL (US); Matthew Boudreau, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 69 days.

(21) Appl. No.: 16/764,103

(22) PCT Filed: Nov. 16, 2018

(86) PCT No.: PCT/US2018/061579
§ 371 (c)(1),
(2) Date: May 14, 2020

(87) PCT Pub. No.: WO2019/099873
PCT Pub. Date: May 23, 2019

(65) Prior Publication Data
US 2020/0276189 A1     Sep. 3, 2020

Related U.S. Application Data

(60) Provisional application No. 62/587,707, filed on Nov. 17, 2017.

(51) Int. Cl.
| | | |
|---|---|---|
| A61K 31/495 | (2006.01) | |
| A61P 35/00 | (2006.01) | |
| A61K 31/4184 | (2006.01) | |
| A61K 31/437 | (2006.01) | |
| A61K 31/4523 | (2006.01) | |
| A61K 31/506 | (2006.01) | |
| A61K 31/517 | (2006.01) | |
| A61K 31/519 | (2006.01) | |
| A61K 31/5377 | (2006.01) | |
| A61K 45/06 | (2006.01) | |

(52) U.S. Cl.
CPC ........ *A61K 31/495* (2013.01); *A61K 31/4184* (2013.01); *A61K 31/437* (2013.01); *A61K 31/4523* (2013.01); *A61K 31/506* (2013.01); *A61K 31/517* (2013.01); *A61K 31/519* (2013.01); *A61K 31/5377* (2013.01); *A61K 45/06* (2013.01); *A61P 35/00* (2018.01)

(58) Field of Classification Search
CPC .. A61K 31/507; A61K 31/437; A61K 31/445; A61P 35/00
See application file for complete search history.

(56) References Cited

U.S. PATENT DOCUMENTS

| | | | |
|---|---|---|---|
| 5,723,459 A | 3/1998 | Armistead et al. | |
| 5,844,001 A | 12/1998 | McClay et al. | |
| 6,251,967 B1 | 6/2001 | Perichaud et al. | |
| 6,303,329 B1 | 10/2001 | Heinrikson et al. | |
| 6,403,765 B1 | 6/2002 | Alnemri | |
| 6,534,267 B1 | 3/2003 | Wang et al. | |
| 6,762,045 B2 | 7/2004 | Krebs et al. | |
| 6,878,743 B2 | 4/2005 | Choong et al. | |
| 7,041,784 B2 | 5/2006 | Wang et al. | |
| 7,632,972 B2 | 12/2009 | Hergenrother et al. | |
| 8,299,057 B2 | 10/2012 | Borgia et al. | |
| 8,592,584 B2 * | 11/2013 | Hergenrother ....... | C07D 211/62 544/360 |
| 8,778,945 B2 | 7/2014 | Hergenrother et al. | |
| 8,916,705 B2 | 12/2014 | Hergenrother | |

(Continued)

FOREIGN PATENT DOCUMENTS

| | | |
|---|---|---|
| CA | 2866021 A1 | 9/2013 |
| CN | 101184491 A | 5/2008 |

(Continued)

OTHER PUBLICATIONS

Peh (Molecular Cancer Therapeutics vol. 15 pp. 1859-1869. Published Aug. 3, 2016). (Year: 2016).*
Cross (Cancer Discovery vol. 4 pp. 1046-1061 published 2014) (Year: 2014).*
"Melanoma: Catching and Curing Skin Cancer—Research Summary," accessed on the internet at https://www. theeagle.com/archives/melanoma-catching-and-curing-skin-cancer—researchsummary/article_85ae6fdb-034f-5921-89be-57d5aeeeb0be.html, retrieved Jun. 8, 2020, 3pgs.
Atefi et al., "Reversing Melanoma Cross-Resistance to BRAF and MEK Inhibitors by Co-Targeting the AKT/mTOR Pathway," PLoS One., 6(12):e28973, Dec. 2011.

(Continued)

*Primary Examiner* — Theodore R. Howell
*Assistant Examiner* — George W Kosturko
(74) *Attorney, Agent, or Firm* — Haukaas Fortius PLLC; Michael Haukaas

(57) ABSTRACT

The discovery of mutant or fusion kinases that drive oncogenesis, and the subsequent approval of specific inhibitors for these enzymes, has been instrumental in the management of some cancers. However, acquired resistance remains a significant problem in the clinic, limiting the long-term effectiveness of most of these drugs. Herein is demonstrated a strategy to overcome this resistance through drug-induced MEK cleavage (via direct procaspase-3 activation) combined with targeted kinase inhibition. This combination effect is shown to be general across diverse tumor histologies (melanoma, lung cancer, and leukemia) and driver mutations (mutant BRAF or EGFR, fusion kinases EML4-ALK and BCR-ABL). Caspase-3-mediated degradation of MEK kinases results in sustained pathway inhibition and substantially delayed or eliminated resistance in cancer cells in a manner superior to combinations with MEK inhibitors. These data suggest the generality of drug-mediated MEK kinase cleavage as a therapeutic strategy to prevent resistance to targeted anticancer therapies.

19 Claims, 21 Drawing Sheets

(56) References Cited

U.S. PATENT DOCUMENTS

| | | | |
|---|---|---|---|
| 9,102,661 B2 | 8/2015 | Hergenrother et al. | |
| 9,249,116 B2 | 2/2016 | Hergenrother et al. | |
| 9,399,035 B2 | 7/2016 | Hergenrother et al. | |
| 9,421,202 B2 | 8/2016 | Hergenrother et al. | |
| 9,522,901 B2 | 12/2016 | Hergenrother et al. | |
| 9,592,229 B2 | 3/2017 | Hergenrother et al. | |
| 9,643,960 B2 | 5/2017 | Hergenrother et al. | |
| 9,663,482 B2 | 5/2017 | Hergenrother et al. | |
| 11,129,830 B2 * | 9/2021 | Hergenrother | A61K 31/506 |
| 2003/0008015 A1 | 1/2003 | Levisage et al. | |
| 2004/0077542 A1 | 4/2004 | Wang et al. | |
| 2004/0180828 A1 | 9/2004 | Shi | |
| 2007/0049602 A1 | 3/2007 | Hergenrother et al. | |
| 2009/0010927 A1 | 1/2009 | Yaffe et al. | |
| 2010/0291214 A1 | 11/2010 | Gabriele et al. | |
| 2011/0257398 A1 | 10/2011 | Hergenrother et al. | |
| 2011/0319390 A1 | 12/2011 | deLong et al. | |
| 2012/0040995 A1 | 2/2012 | Hergenrother et al. | |
| 2012/0077834 A1 | 3/2012 | Castro et al. | |
| 2012/0178803 A1 | 7/2012 | Harn et al. | |
| 2014/0348819 A1 | 11/2014 | Golub et al. | |
| 2015/0017264 A1 | 1/2015 | Hergenrother et al. | |
| 2015/0231132 A1 | 8/2015 | Hergenrother | |
| 2016/0346277 A1 | 12/2016 | Hergenrother et al. | |
| 2017/0042886 A1 | 2/2017 | Hergenrother et al. | |
| 2017/0105989 A1 | 4/2017 | Hergenrother et al. | |

FOREIGN PATENT DOCUMENTS

| | | | | |
|---|---|---|---|---|
| CN | 104507479 A | 4/2015 | | |
| JP | 2007513962 A | 5/2007 | | |
| JP | 2008545718 A | 12/2008 | | |
| JP | 2012526824 A | 11/2012 | | |
| JP | 2015509965 A | 4/2015 | | |
| RU | 2360692 C1 | 7/2009 | | |
| RU | 2408584 C2 | 1/2011 | | |
| RU | 2410389 C2 | 1/2011 | | |
| RU | 2438695 C2 | 1/2012 | | |
| WO | 2006128173 A2 | 11/2006 | | |
| WO | 2007033374 A2 | 3/2007 | | |
| WO | 2007137200 A2 | 11/2007 | | |
| WO | 2008134474 A3 | 1/2009 | | |
| WO | 2009089508 A1 | 7/2009 | | |
| WO | 2010091382 A1 | 8/2010 | | |
| WO | 2010091383 A2 | 8/2010 | | |
| WO | 2010132440 A2 | 11/2010 | | |
| WO | 2010138141 A1 | 12/2010 | | |
| WO | 2010151746 A2 | 12/2010 | | |
| WO | 2012118978 A1 | 9/2012 | | |
| WO | 2013134398 A1 | 9/2013 | | |
| WO | 2013134407 A2 | 9/2013 | | |
| WO | 2013134407 A3 | 9/2013 | | |
| WO | 2014072357 A1 | 5/2014 | | |
| WO | 2014138279 A1 | 9/2014 | | |
| WO | 2014193898 A1 | 12/2014 | | |
| WO | 2015004636 A1 | 1/2015 | | |
| WO | 2016197129 A1 | 12/2016 | | |
| WO | WO-2016197129 A1 * | 12/2016 | | A61K 31/519 |

OTHER PUBLICATIONS

Botham et al., "Small-Molecule Procaspase-3 Activation Sensitizes Cancer to Treatment with Diverse Chemotherapeutics," ACS Cent Sci., 2(8):545-559, Aug. 2016.
Botham et al., "Small-Molecule Procaspase-3 Activation Sensitizes Cancer to Treatment with Diverse Chemotherapeutics," ACS Cent Sci., 2(8):545-559, Aug. 2016, Supporting Information.
Broecker-Preuss et al., "Sorafenib Inhibits Intracellular Signaling Pathways and Induces Cell Cycle Arrest and Cell Death in Thyroid Carcinoma Cells Irrespective of Histological Origin or BRAF Mutational Status," BMC Cancer, 15(1):184, Dec. 2015.
Cai et al., "Tamoxifen Inhibits Nitrobenzylthioinosine-Sensitive Equilibrative Uridine Transport in Human MCF-7 Breast Cancer Cells," Biochem J., 320(Pt 3):991-995, Dec. 1996.
Caplus, Procaspase, Jun. 2015, 7pgs.
Caplus, Temozolomide (L) Procaspase-1, Apr. 2016, 1pg.
Chen et al., "Caspases and Inhibitor of Apoptosis Proteins in Cutaneous and Mucosal Melanoma: Expression Profile and Clinicopathologic Significance," Hum Pathol., 40(7):950-956, Jul. 2009.
Das Thakur et al., "Modelling Vemurafenib Resistance in Melanoma Reveals a Strategy to Forestall Drug Resistance," Nature, 494(7436):251-255, Feb. 2013.
Dawson James Securities, Institutional Research: Health Care and Technology Industry Note, "Comparative Oncology: A New 'Breed' of Trial Set to Improve Clinical Success in Oncology," Dec. 8, 2015, 19pgs.
Extended Search Report of the EPO dated Nov. 20, 2017 in EP Application No. 17180400.8; 5pgs.
Extended Search Report of the EPO dated Sep. 24, 2015 in EP Application No. 13758061.9; 5pgs.
Golub et al., "Molecular Classification of Cancer: Class Discovery and Class Prediction by Gene Expression Monitoring," Science, 286(5439):531-537, Oct. 1999.
Ho et al., "Acquired BRAF V600E Mutation as Resistant Mechanism after Treatment with Osimertinib," J Thorac Oncol., 12(3):567-572, Mar. 2017.
International Preliminary Report on Patentability for PCT/US2013/029391 dated Sep. 18, 2014, 5pgs.
International Preliminary Report on Patentability for PCT/US2013/029405 dated Sep. 18, 2014, 7pgs.
International Search Report and Written Opinion of the ISA/RU in PCT/US2013/029391 dated Jun. 14, 2013; 2pgs.
International Search Report and Written Opinion of the ISA/RU in PCT/US2013/029405, dated Aug. 15, 2013; 9pgs.
International Search Report and Written Opinion of the ISA/US in PCT/US2016/036063, dated Sep. 14, 2016; 15pgs.
International Search Report and Written Opinion of the ISA/US in PCT/US2018/061579, dated Feb. 1, 2019; 9pgs.
Joseph et al., "The RAF Inhibitor PLX4032 Inhibits ERK Signaling and Tumor Cell Proliferation in a V600E BRAF-Selective Manner," Proc Natl Acad Sci U S A., 107(33):14903-14908, Aug. 2010.
Larkin et al., "Combined Vemurafenib and Cobimetinib in BRAF-Mutated Melanoma," N Engl J Med., 371(20):1867-1876, Nov. 2014.
Lori et al., "Doxorubicin and Cyclophosphamide for the Treatment of Canine Lymphoma: A Randomized, Placebo-controlled Study," Vet Comp Oncol., 8(3):188-195., Sep. 2010.
Martin et al., "Concurrent MEK and Autophagy Inhibition Is Required to Restore Cell Death Associated Danger-Signalling in Vemurafenib-Resistant Melanoma Cells," Biochem Pharmacol., 93(3):290-304, Feb. 2015.
Medline, "Cancer," accessed on the internet at http://www.nlm.nih.gov/medlineplus/cancer; retrieved Mar. 19, 2017; 14pgs.
Patel et al., "Expression of Executioner Procaspases and Their Activation by a Procaspase-Activating Compound in Chronic Lymphocytic Leukemia Cells," Blood, 125(7):1126-1136, Feb. 2015.
Peng et al. "The Inhibition of PAC-1,L-OHP and PAC-1 plus L-OHP on the Human Colorectal Cancer Cell" Zhongguo Putong Waike Zazhi,19(10):1097-1102, Oct. 2010.
Peterson et al., "Discovery and Canine Preclinical Assessment of a Nontoxic Procaspase-3-Activating Compound," Cancer Research, 70:7232-7241, Sep. 2010.
Peterson et al., "PAC-1 Activates Procaspase-3 in Vitro through Relief of Zinc-Mediated Inhibition," J. Mol. Biol., 388:144-158, Mar. 2009.
Peterson et al., "Procaspase-3 Activation as an Anti-Cancer Strategy: Structure-Activity Relationship of Procaspase-Activating Compound 1 (PAC-1) and Its Cellular Co-Localization with Caspase-3," J. Med. Chem.,59:5721-5731, Aug. 2009.
Putt et al., "Small-molecule Activation of Procaspase-3 to Caspase-3 as a Personalized Anticancer Strategy," Nat. Chem. Biol., 2(10):543-550, Oct. 2006.
Rasheed et al., "Cyclodextrins as Drug Carrier Molecule: A Review.," Sci Pharm., 76(4):567-598, Nov. 2008.

(56) References Cited

OTHER PUBLICATIONS

Razi et al. "Paclitaxel Cytotoxicity is Significantly Enhanced by a Novel Pro-apoptotic Agent in the Treatment of Nonsmall Cell Lung Cancer." J. American College of Surgeons, 213(3) Suppl 1, pp. S42, Sep. 2011.
Robert et al., "Improved Overall Survival in Melanoma with Combined Dabrafenib and Trametinib," N Engl J Med, 372(1):30-39, Jan. 2015.
Rowe et al., "Handbook of Pharmaceutical Excipients," 5th Ed.; Royal Pharmaceutical Society of Great Britain; pp. 217-221; 2006.
Ryu et al., "Therapeutic Inhibitors against Mutated BRAF and MEK for the Treatment of Metastatic Melanoma," Chonnam Med J., 53(3):173-177, Sep. 2017.
Smith, Cancer Treatment from a Vet, accessed on the internet at http://blogs.www.redorbit.com/author/smith, retrieved Feb. 28, 2015, 3pgs.
STN CAS RN 1103440 60 3 entered Feb. 9, 2009.
Sweetlove et al., "Inhibitors of Pan-PI3K Signaling Synergize with BRAF or MEK Inhibitors to Prevent BRAF-Mutant Melanoma Cell Growth," Front Oncol., 5(135):1-14, Jun. 2015.
Temozoloamide Product Specification, accessed on the internet at http://www.cancer.gov/cancertopics/druginfo/temozolomide/print, downloaded Mar. 25, 2015, 2pgs, Oct. 2006.
Wang et al. "A Novel Small-Molecule Activator of Procaspase-3 Induces Apoptosis in Cancer Cells and Reduces Tumor Growth in Human Breast, Liver and Gallbladder Cancer Xenografts," Mol Oncol., 8(8):1640-1652, Dec. 2014.
Wolan et al., "Small-Molecule Activators of a Proenzyme," Science, 326(5954):853-858, Nov. 2009.
Yang et al., "The p53-dependent Apoptotic Pathway of Breast Cancer Cells (BC-MI) Induced by the bis-type Bioreductive Compound Aziridinylnaphthoquinone," Breast Cancer Res., 7(1):RI9-R27, Epub Nov. 4, 2004.
Zorn et al., "Self-Assembling Small Molecules Form Nanofibrils That Bind Procaspase-3 To Promote Activation," J Am Chem Soc., 133(49):19630-19633, Nov. 2011.
Extended Search Report of the European Patent Office dated Dec. 13, 2021 in EP Application No. 18879684.1; 16pgs.
Hrustanovic et al., "RAS-MAPK Dependence Underlies a Rational Polytherapy Strategy in EML4-ALK-Positive Lung Cancer," Nat Med., 21(9):1038-1047, Sep. 2015.
Ardini et al., "Entrectinib, a Pan-TRK, ROS1, and ALK Inhibitor with Activity in Multiple Molecularly Defined Cancer Indications," Mol Cancer Ther., 15(4):628-639, Apr. 2016.
Aveic et al., "Combating Autophagy Is a Strategy to Increase Cytotoxic Effects of Novel ALK Inhibitor Entrectinib in Neuroblastoma Cells," Oncotarget, 7(5):5646-5563, Feb. 2016.
Boudreau et al., "Procaspase-3 Overexpression in Cancer: A Paradoxical Observation with Therapeutic Potential," ACS Chem. Biol., 14(11):2335-2348, Jul. 2019.

Buder et al., "Systemic Treatment of Metastatic Uveal Melanoma: Review of Literature and Future Perspectives," Cancer Med., 2(5):674-686, Oct. 2013.
Chen et al., "Signaling Pathways and Potential Molecular Targets in Uveal Melanoma," Retrieved from the Internet at https://smjournals.com/ebooks/management-of-malignant-melanoma/chapters/, Jul. 2017.
Drilon et al., "Safety and Antitumor Activity of the Multitargeted Pan-TRK, ROS1, and ALK Inhibitor Entrectinib: Combined Results from Two Phase I Trials (ALKA-372-001 and STARTRK-1)," Cancer Discov., 7(4):400-409, Apr. 2017.
Feng et al., "A Platform of Synthetic Lethal Gene Interaction Networks Reveals that the GNAQ Uveal Melanoma Oncogene Controls the Hippo Pathway through FAK," Cancer Cell, 35(3):457-472, Mar. 2019.
Huang et al., "Predicting Drug Combination Index and Simulating the Network-Regulation Dynamics by Mathematical Modeling of Drug-Targeted EGFR-ERK Signaling Pathway," Sci. Rep., 7:40752, Jan. 2017.
International Search Report and Written Opinion of the ISA/US in PCT/US2019/054500, dated Dec. 18, 2019; 12pgs.
Kaliki et al., "Uveal Melanoma: Relatively Rare but Deadly Cancer," Eye (Lond)., 31(2):241-257, Feb. 2017.
Kfoury et al., "AMPK Promotes Survival of C-Myc-Positive Melanoma Cells by Suppressing Oxidative Stress," EMBO J., 37(5):e97673, Mar. 2018.
Lu et al., "Cetuximab Reverses the Warburg Effect by Inhibiting HIF-1-Regulated LDH-A," Mol Cancer Ther., 12(10):2187-2199, Oct. 2013.
Luke et al., "Biology of Advanced Uveal Melanoma and Next Steps for Clinical Therapeutics," Pigm Cell Melanoma Res., 28(2):135-147, Mar. 2015.
Menichincheri et al., "Discovery of Entrectinib: A New 3-Aminoindazole As a Potent Anaplastic Lymphoma Kinase (ALK), c-ros Oncogene 1 Kinase (ROS1), and Pan-Tropomyosin Receptor Kinases (Pan-TRKs) inhibitor," J Med Chem., 59(7):3392-3408, Apr. 2016.
Partial Search Report of the European Patent Office dated Aug. 9, 2021 in EP Application No. 18879684.1; 15pgs.
Patel et al., "Therapeutic Implications of the Emerging Molecular Biology of Uveal Melanoma," Clin Cancer Res., 17(8):2087-2100, Apr. 2011.
Peh et al., "Overcoming Resistance to Targeted Anticancer Therapies through Small-Molecule-Mediated MEK Degradation," Cell Chem Biol., 25(8):996-1005, Aug. 2018.
Peh et al., "The Combination of Vemurafenib and Procaspase-3 Activation Is Synergistic in Mutant BRAF Melanomas," Mol Cancer Ther., 15(8):1859-1869, Aug. 2016.
Zheng et al., "Inhibitory Effect of of Pyrvinium Pamoate on Uveal Melanoma Cells Involves Blocking of Wnt/β-Catenin Pathyway," Acta Biochim Biophys Sin (Shanghai)., 49(10):890-898, Oct. 2017.

* cited by examiner

CANCER THERAPY BY DEGRADING DUAL MEK SIGNALING

RELATED APPLICATIONS

This application is a National Stage filing under 35 U.S.C. § 371 of International Application No. PCT/US2018/061579 filed Nov. 16, 2018, which claims priority under 35 U.S.C. § 119(e) to U.S. Provisional Patent Application No. 62/587,707, filed Nov. 17, 2017, which applications are incorporated herein by reference.

GOVERNMENT SUPPORT

This invention was made with government support under Grant No. R01-CA120439 awarded by the National Institutes of Health. The government has certain rights in the invention.

BACKGROUND OF THE INVENTION

Overexpression, mutation, or fusion of kinases that affect cell proliferation and survival pathways drive tumorigenesis in numerous cancers. Specific targeting of these oncogenic kinases with inhibitors has led to dramatic responses in large fractions of patients with advanced disease. However, response to kinase inhibitors is often short-lived due to the rapid onset of resistance to these drugs. Various resistance mechanisms exist to reactivate the cell proliferation and survival pathways. In particular, reactivation of the mitogen-activated protein kinase (MAPK) pathway is responsible for acquired resistance to a large number of clinically approved inhibitors, including those targeting mutant BRAF, mutant EGFR, EML4-ALK, or BCR-ABL kinases.

Recognizing that reactivation of the MAPK pathway diminishes the clinical efficacy of kinase inhibitors, and that MEK1/2 kinases are the ultimate gatekeeper kinases of the MAPK pathway, upfront combination therapy with a MEK1/2 inhibitor (e.g. trametinib or cobimetinib) has been investigated with several classes of kinase inhibitors in an effort to delay resistance. Clinically, the combination of MEK1/2 and mutant BRAF inhibitors extends progression-free and overall survival in the treatment of metastatic BRAF$^{V600E}$ melanomas. However, resistance to this dual therapy invariably occurs after a year of therapy initiation, in part due to secondary mutations on MEK1 and MEK2 kinases that abolish anticancer efficacy.

Accordingly, the loss of anticancer efficacy caused by secondary mutations to MEK1 and MEK2 can be addressed by a small molecule approach that degrades MEK1 and MEK2 kinases to render them incapable of downstream signaling, and therefore would provide an advancement in cancer therapy.

SUMMARY

The clinical utility of targeted anticancer therapies is limited by the rapid onset of resistance. In drug-resistant clones, reactivation of downstream signaling via MEK1/2 kinases is often observed, thus inhibition of MEK1/2 has become an attractive strategy to delay resistance; however, drug-mediated MEK1/2 inhibition provides only temporary shutdown of downstream signaling and modest survival benefit. As a promising anticancer strategy, drug-induced degradation of MEK1 and MEK2 is shown herein to broadly enhance the cell death mediated by a diverse set of approved kinase inhibitors, including for melanoma, lung cancer, and leukemia. This loss of MEK1 and MEK2 leads to sustained inhibition of downstream signaling, dramatically delaying or eliminating the onset of resistance in cancer cells.

Accordingly, this disclosure provides a composition comprising:

(a) the compound PAC-1:

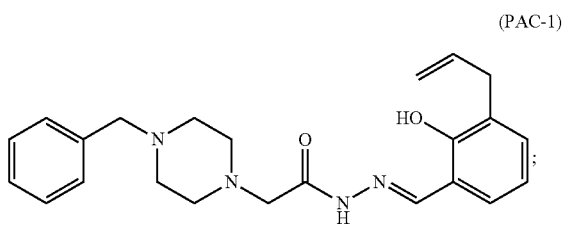 [SMILES: C=CCc1cccc(/C=N/NC(=O)CN2CCN(Cc3ccccc3)CC2)c1O]

(PAC-1)

(b) at least one second active agent, wherein the second active agent is an inhibitor of a mutant kinase or an inhibitor of a fusion kinase; and
(c) optionally a pharmaceutically acceptable diluent, excipient, carrier, or a combination thereof.

This disclosure also provides a method of treating a cancer comprising administering to a patient in need thereof, concurrently or sequentially, a therapeutically effective amount of the compound PAC-1, and an effective amount of a second active agent, wherein the second active agent is an inhibitor of a mutant kinase or an inhibitor of a fusion kinase; wherein the cancer is thereby treated.

Additionally, this disclosure provides the use of a composition to prepare a medicament for the treatment of cancer, the composition comprising:

(a) the compound PAC-1;
(b) at least one second active agent, wherein the second active agent is an inhibitor of a mutant kinase or an inhibitor of a fusion kinase; and
(c) optionally a pharmaceutically acceptable diluent, excipient, carrier, or combination thereof;

wherein the composition is an enhancer of MEK kinase degradation.

The disclosed methods provide for the use of the compositions described herein for use in medical therapy. The medical therapy can be treating cancer, for example, melanoma, leukemia, breast cancer, lung cancer, pancreatic cancer, prostate cancer, or colon cancer. The invention also provides for the use of a composition as described herein for the manufacture of a medicament to treat a disease in a mammal, for example, cancer in a human, cat, or dog. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

Figure 9:
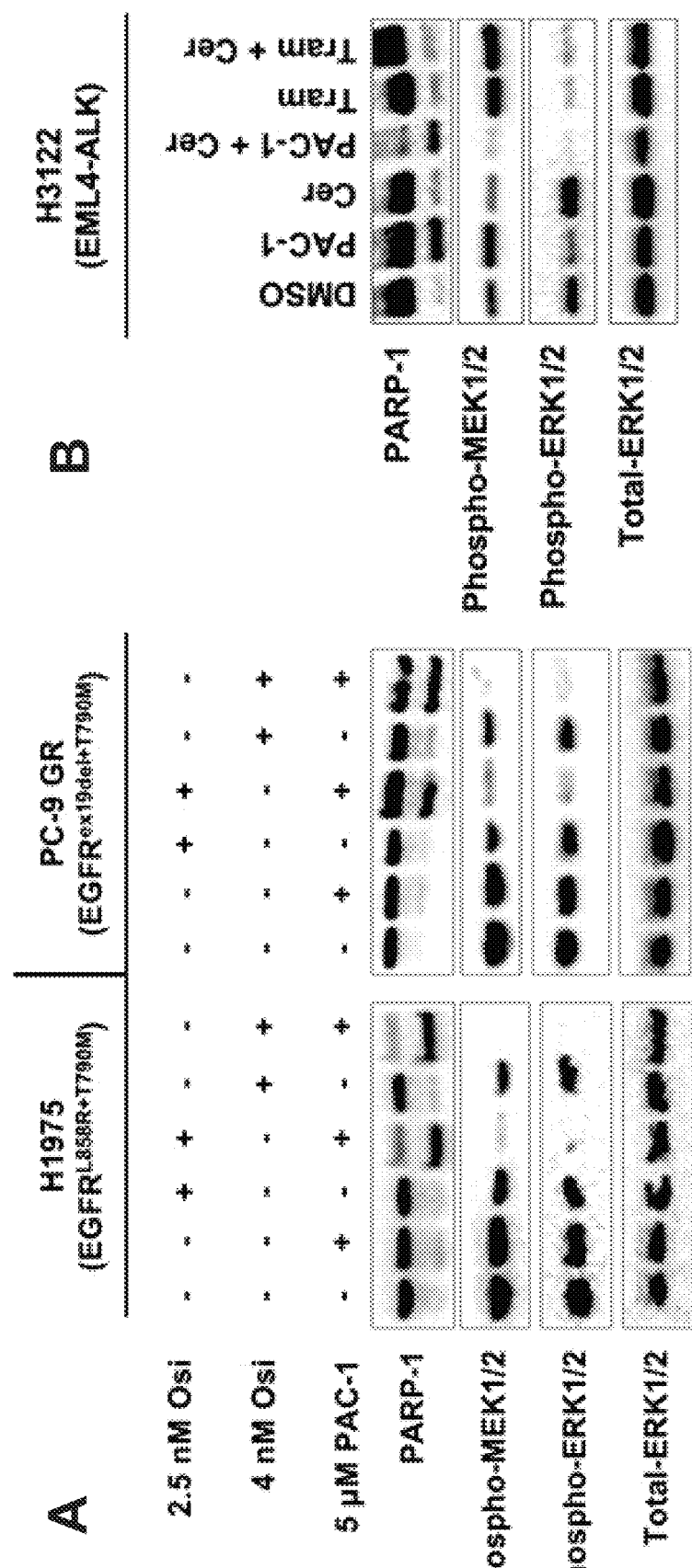
Figure 9:
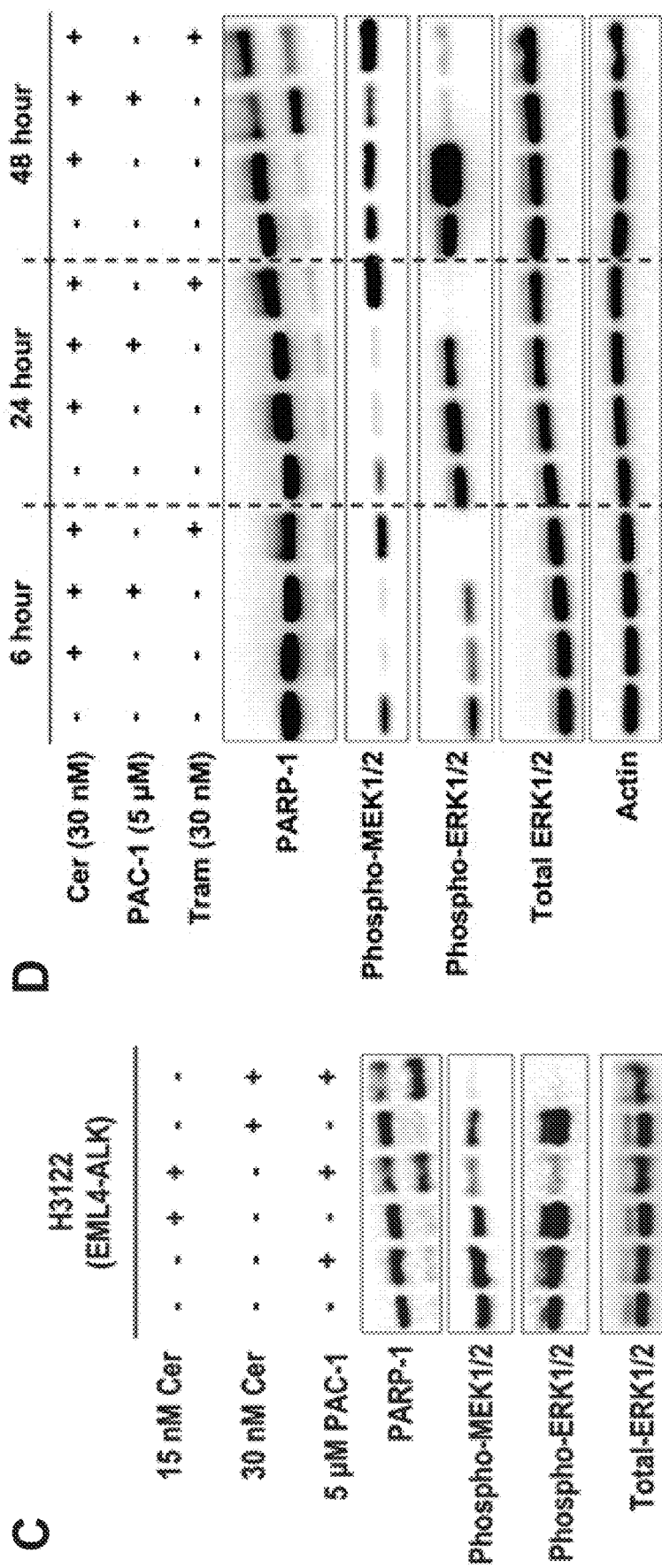
Figure 9:
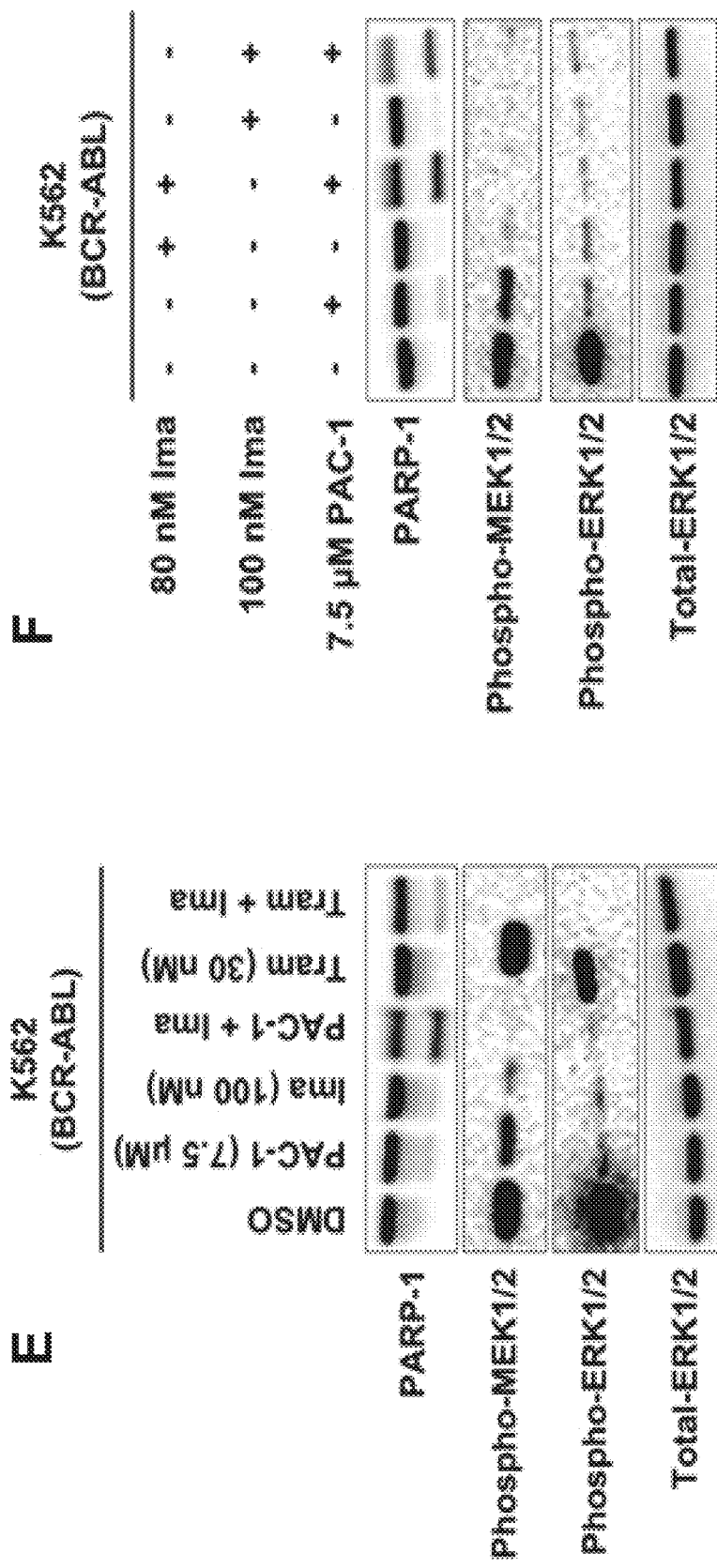

FIG. 9. Sustained inhibition of MEK1/2 and ERK1/2 phosphorylation. Related to FIG. 3. (A) MEK1/2 and ERK1/2 phosphorylation in EGFR$^{T790M}$ cells after 48 hour of treatment with PAC-1 and lower concentration of osimertinib (2.5 nM). (B-D) PAC-1+ceritinib lead to sustained MEK1/2 phosphorylation in H3122 cells. (B) H3122 cells treated with PAC-1 (5 µM)+ceritinib (30 nM) for 48 hours led to sustained inhibition of MEK1/2 and ERK1/2 phosphorylation. However, trametinib (30 nM)+ceritinib treatment did not inhibit MEK1/2 phosphorylation. (C) At a lower concentration of ceritinib (15 nM), the combination led to sustained inhibition of MEK1/2 and ERK1/2 phosphorylation. (D) Timecourse of phospho-MEK1/2 and phospho-ERK1/2 inhibition. H3122 cells were treated with DMSO, ceritinib, ceritinib+PAC-1 or ceritinib+trametinib for 6, 24, or 48 hours. Little or no inhibition of MEK1/2 phosphorylation was observed with trametinib co-treatment. (E-F) Inhibition of MEK1/2 and ERK1/2 phosphorylation in K-562 (BCR-ABL) cells. (E) K-562 cells treated with PAC-1+ceritinib for 48 hours led to sustained inhibition of MEK1/2 and ERK1/2 phosphorylation. Unlike the BRAF$^{V600E}$, EGFR$^{T790M}$, and EML4-ALK cells, activation of procaspase-3 was observed in cells treated with imatinib+trametinib, leading to sustained inhibition of MEK1/2 and ERK1/2 phosphorylation. (F) At a lower concentration of imatinib (80 nM), the combination led to sustained inhibition of MEK1/2 and ERK1/2 phosphorylation.

Figure 4:
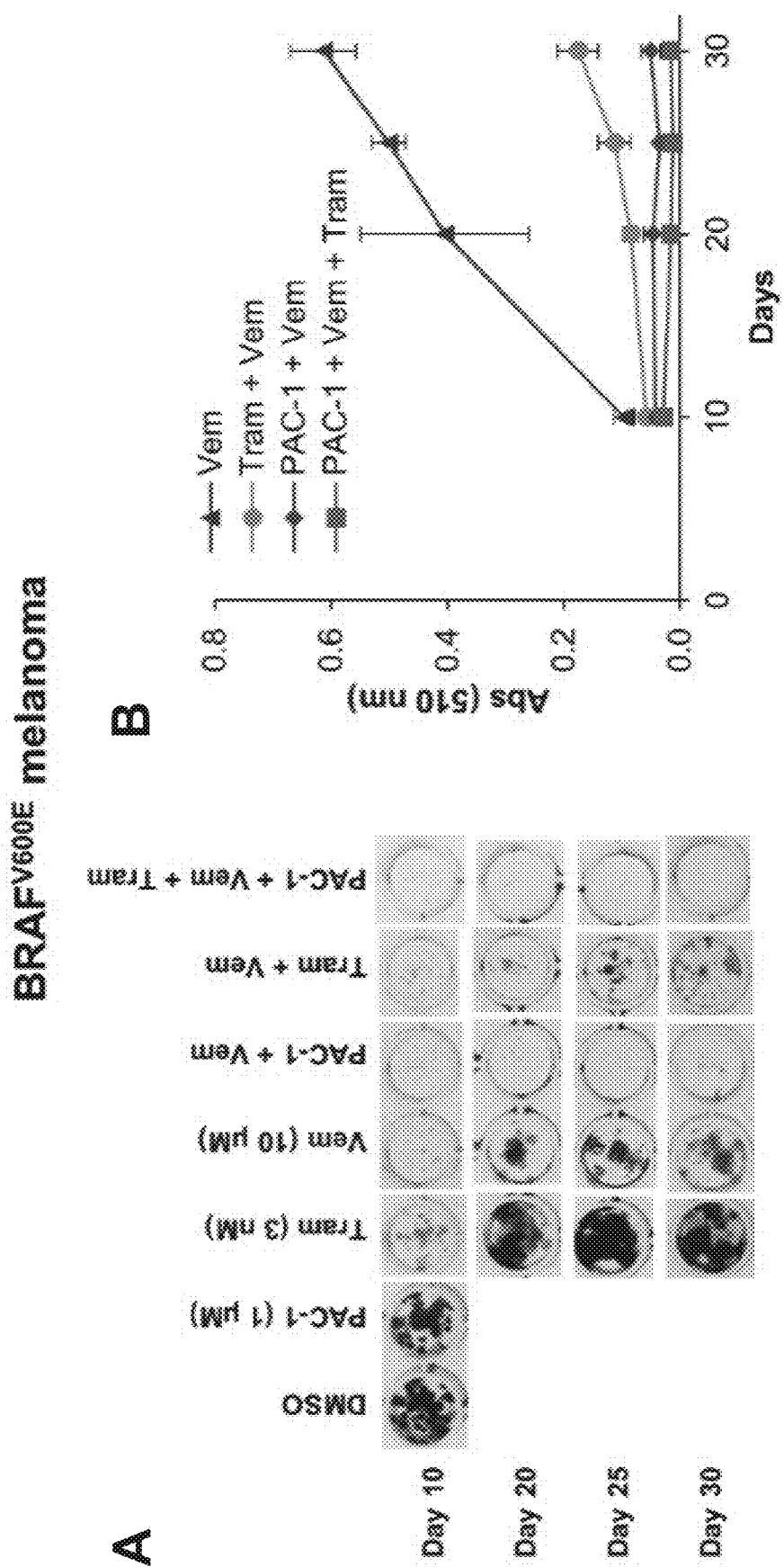
FIG. 4. PAC-1 combination therapies substantially delay or eliminate acquired resistance. (A) A375 cells were treated with indicated concentrations of PAC-1, vemurafenib, trametinib, or the respective combinations for up to 30 days. Cells were fixed and stained with SRB dye before imaging. (B) Quantification of (A), data reported is the mean and standard error of three independent experiments. (C) PC-9 GR cells were treated with indicated concentrations of PAC-1, osimertinib, trametinib, or the respective combinations for up to 35 days. Cells were imaged as described in (B). See also FIG. 10. (D) Quantification of (C), data reported is the mean and standard error of two independent experiments. (E) H3122 cells were treated with indicated concentrations of PAC-1, ceritinib, trametinib, or the respective combinations for up to 32 days. Image shown is representative of two independent experiments. (F) Zoom in view of H3122 cells treated PAC-1+ceritinib, or trametinib+ ceritinib for 32 days. Visibly more resistant colonies were seen in cells treated to trametinib+ceritinib compared to PAC-1+ceritinib.
Figure 4:
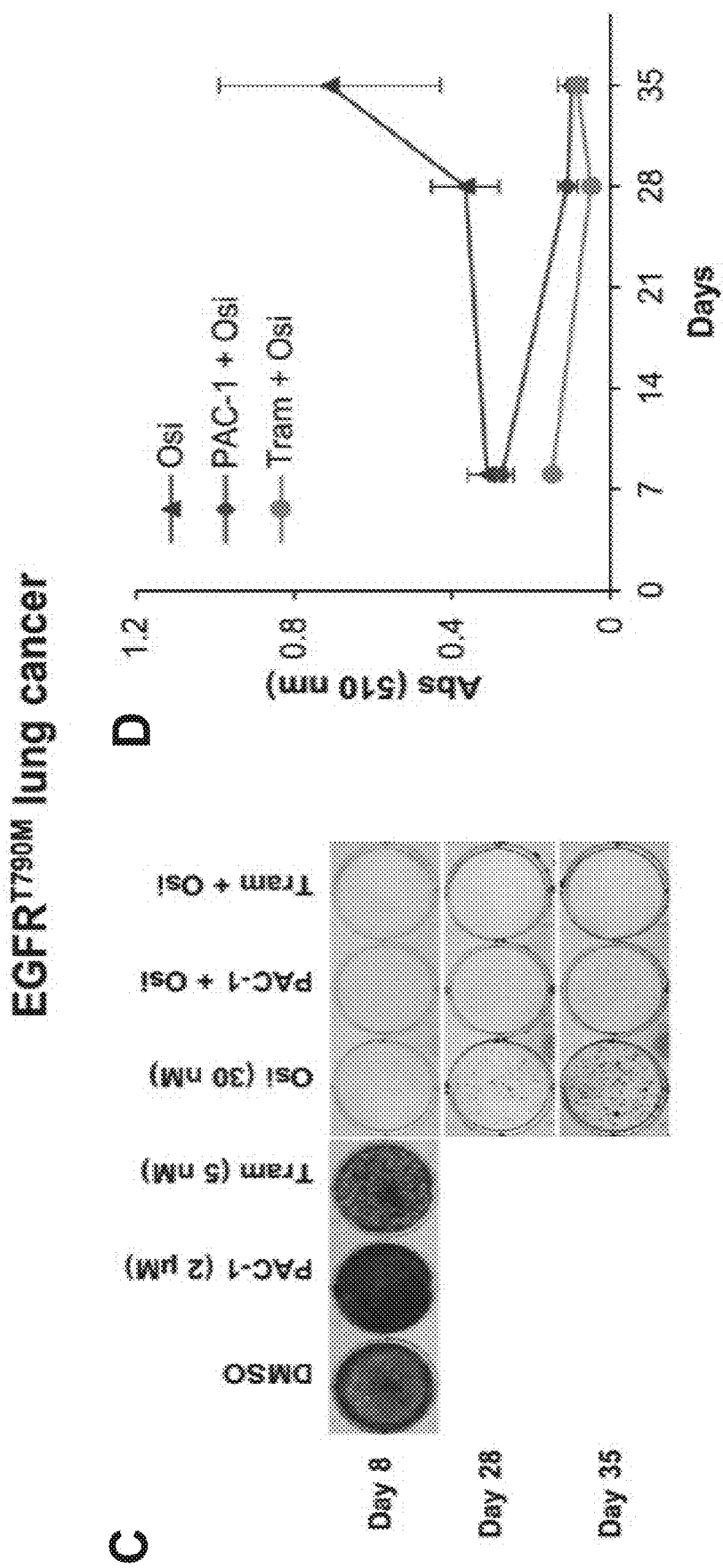
Figure 4:
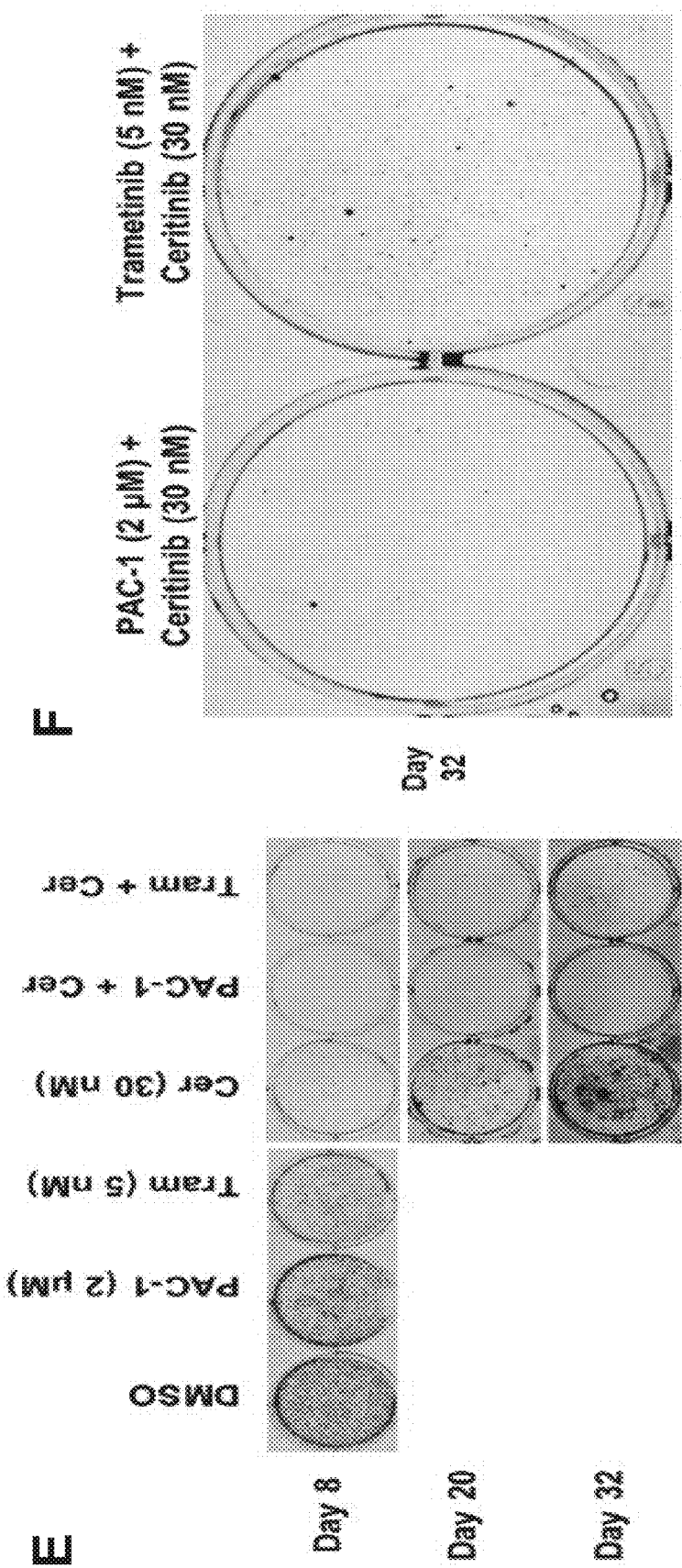
Figure 10:
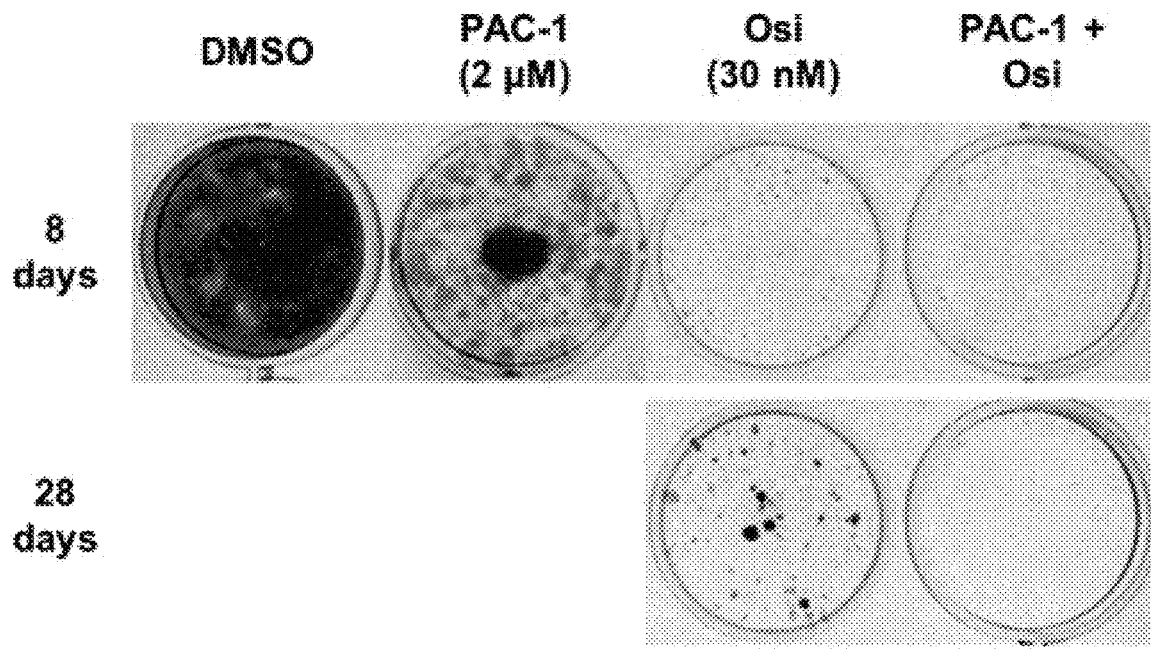
Figure 10:
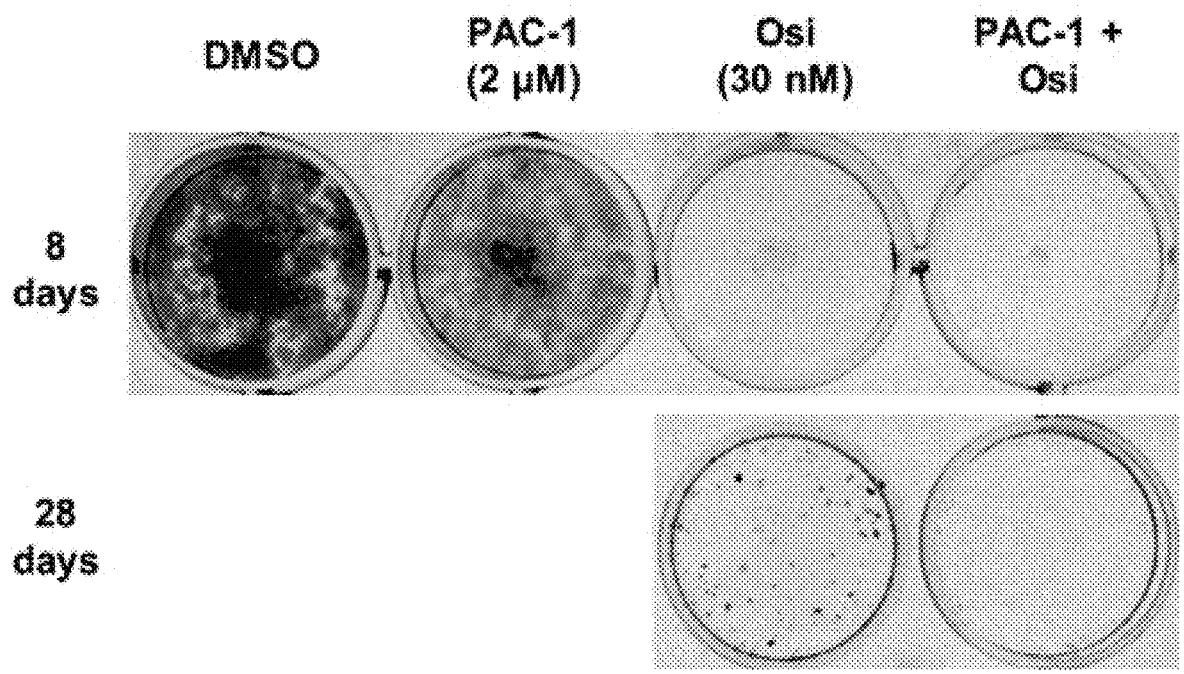

FIG. 10. PAC-1+osimertinib delays resistance. Related FIG. 4. (A) PC-9 GR cells and (B) H1975 cells following 28 days of treatment. Cells were fixed and stained with SRB dye before imaging.

Figure 11:
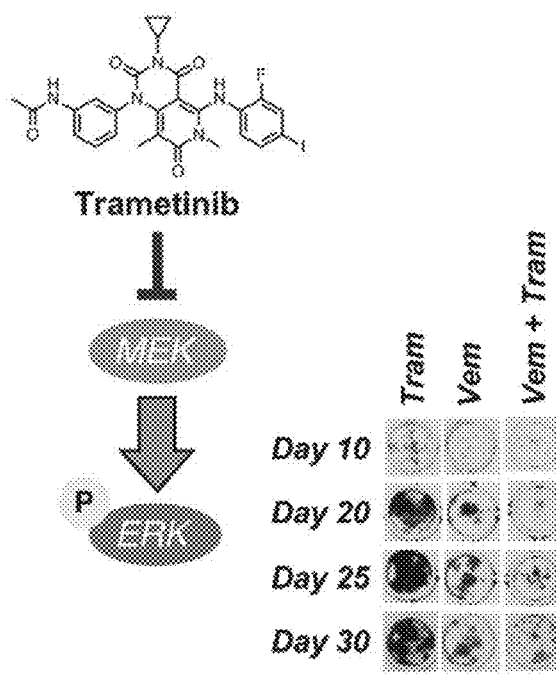
Figure 11:
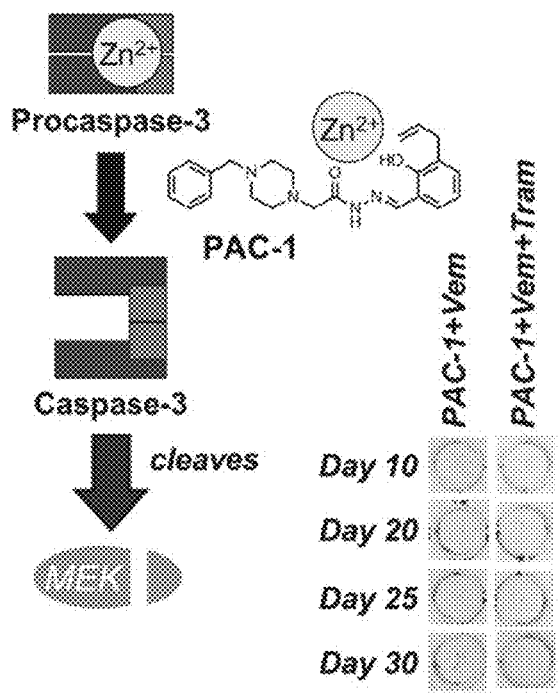

FIG. 11. Rapid onset of resistance to targeted kinase inhibitors limits their use in treating advanced cancers. This disclosure shows that combination of diverse kinase inhibitors with a procaspase-3 activating compound (PAC-1) leads to degradation of MEK1/2, dramatically delaying acquired resistance; wherein PAC-1 enhances caspase-3 activity and apoptosis induced by diverse kinase inhibitors; Caspase-3-mediated MEK degradation sustains inhibition of MEK phosphorylation; PAC-1 combination therapies dramatically delay or eliminate acquired resistance.

DETAILED DESCRIPTION

Given the transient and differential inhibition of MEK1/2 activity with the clinically used inhibitors, a hypothesis was formulated that combination therapy with a small molecule capable of inducing enzymatic degradation of MEK1/2 kinases would have an advantage over direct inhibition, resulting in low-or-no resistance when used with a wide range of clinically approved kinase inhibitors. Detailed proteomics experiments have shown that MEK1/2 kinases are cleaved by caspase-3 during apoptosis, and it has been widely reported that procaspase-3 is overexpressed in a variety of cancers relative to healthy tissues. While evasion of apoptosis, through a variety of mechanisms, is regarded as a hallmark of cancer, previous studies suggested that overexpression of procaspase-3 can drive oncogenesis. These observations imply that activation of procaspase-3 to caspase-3 and subsequent caspase-3 mediated degradation of MEK can occur selectively in cancer cells relative to healthy cells. An additional advantage of direct procaspase-3 activation is the ability to bypass defects in the apoptotic circuitry commonly found upstream of procaspase-3 in cancer cells (FIG. 11).

PAC-1 is a selective procaspase-3 activating compound that synergizes with vemurafenib, a BRAF$^{V600E}$ inhibitor, in numerous melanoma cell lines harboring the V600E mutation in BRAF to delay onset of acquired resistance, suggesting the feasibility of this strategy. Herein is assessed PAC-1 in combination with four different clinically approved inhibitors targeting four different kinases that signal through the MAPK pathway. These combinations dramatically enhance caspase-3 activity and induce degradation of MEK1/2 kinases. Herein is reported that adding PAC-1 to kinase inhibitors targeting BRAF$^{V600E}$ (vemurafenib), EGFR$^{T790M}$ (osimertinib), EML4-ALK (ceritinib), or BCR-ABL (imatinib) enhances MEK1 and MEK2 degradation, leading to durable inhibition of MEK1/2 and ERK1/2 phosphorylation, enhanced apoptotic cell death, and markedly delayed or eliminated acquired resistance. As PAC-1 is currently being evaluated in clinical trials in human cancer patients (NCT02355535, NCT03332355), the results presented herein can be rapidly translated to combination clinical trials with the various targeted kinase inhibitors, studies that could provide significant benefit to cancer patients.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

The term "concurrently" means (1) simultaneously in time, or (2) at different times during the course of a common treatment schedule.

The term "sequentially" refers to the administration of one active agent used in the method followed by administration of another active agent. After administration of one active agent, the next active agent can be administered substantially immediately after the first, or the next active agent can be administered after an effective time period after the first active agent; the effective time period is the amount of time given for realization of maximum benefit from the administration of the first active agent.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art, especially in light of the detailed disclosure provided herein. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

In one embodiment, an effective amount refers to an amount of the active agent described herein that are effective, either alone or in combination with a pharmaceutical carrier, upon single- or multiple-dose administration to a cell or a subject, e.g., a patient, at inhibiting the growth or proliferation, inducing the killing, or halting the growth of hyperproliferative cells. Such growth inhibition or killing can be reflected as a prolongation of the survival of the subject, e.g., a patient beyond that expected in the absence of such treatment, or any improvement in the prognosis of the subject relative to the absence of such treatment.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

The compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting. Additionally, the terms "induce," "inhibit," "potentiate," "elevate," "increase," "decrease," or the like denote quantitative differences between two states, and can refer to at least statistically significant differences between the two states. For example, "an amount effective to inhibit the growth of hyperproliferative cells" means that the rate of growth of the cells can be, in some embodiments, at least statistically significantly different from the untreated cells. Such terms can be applied herein to, for example, rates of proliferation.

The phrase "inhibiting the growth or proliferation" of the hyperproliferative cell, e.g. neoplastic cell, refers to the slowing, interrupting, arresting, or stopping its growth and metastasis, and does not necessarily indicate a total elimination of the neoplastic growth.

The term "cancer" generally refers to any of a group of more than 100 diseases caused by the uncontrolled growth of abnormal cells. Cancer can take the form of solid tumors and lymphomas, and non-solid cancers such as leukemia. Unlike normal cells, which reproduce until maturation and then only as necessary to replace wounded cells, cancer cells can grow and divide endlessly, crowding out nearby cells and eventually spreading to other parts of the body. Examples of some cancerous conditions that are can be treated include, but are not limited to, anal cancer, transitional cell bladder cancer, bone cancer, breast cancer, cervical cancer, colorectal cancer, gastric cancer, head and neck cancer, Kaposi's sarcoma, leukemia, lung cancer such as bronchogenic lung cancer, small cell lung cancer, and non-small cell lung cancer, Hodgkin's lymphoma, Non-Hodgkin's lymphoma, malignant lymphoma, neuroblastomas, osteogenic carcinomas (e.g. cancer of the bone), ophthalmic cancers (e.g. retinoblastomas and other cancers of the eye), ovarian cancer, prostate cancer, renal cancer, skin cancers such as melanoma, soft tissue sarcomas, thyroid cancer, and Wilms' tumor. Other examples of non-malignant hyperproliferative conditions (e.g. precancerous conditions) that are within the scope of the invention include, but are not limited to, adenomas, chondromas, enchondromas, fibromas, myomas, myxomas, neurinomas, osteoblastomas, osteochondromas, osteomas, papillary tumors, and the like, including other cancers described herein.

The terms "leukemia" or "leukemic cancer" refer to all cancers or neoplasias of the hematopoetic and immune systems (blood and lymphatic system). These terms refer to a progressive, malignant disease of the blood-forming organs, marked by distorted proliferation and development of leukocytes and their precursors in the blood and bone marrow. Myelomas refer to other types of tumors of the blood and bone marrow cells. Lymphomas refer to tumors of the lymph tissue. Examples of leukemia include acute myelogenous leukemia (AML), acute lymphoblastic leukemia (ALL), and chronic myelogenous leukemia (CML).

Embodiments of the Invention

This disclosure provides various embodiments of a composition comprising:

(a) the compound PAC-1:

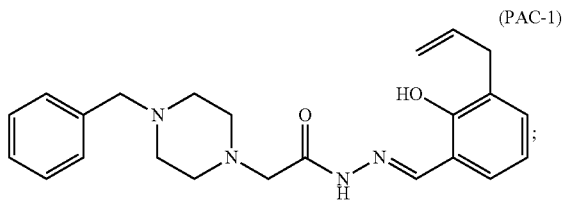 [SMILES: C=CCc1cccc(/C=N/NC(=O)CN2CCN(Cc3ccccc3)CC2)c1O]

(PAC-1)

(b) at least one second active agent, wherein the second active agent is an inhibitor of a mutant kinase or an inhibitor of a fusion kinase; and (c) optionally a pharmaceutically acceptable diluent, excipient, carrier, or a combination thereof. In other addition embodiments of this disclosure, the second active agent is an inhibitor of mutant c-kit.

In various embodiments of this disclosure, the composition is an enhancer of MEK kinase degradation. In various other embodiments, the composition is a mediator of caspase-3 degradation of both MEK-1 and MEK-2 kinases. In additional embodiments, the composition is an inhibitor of MEK-1 and MEK-2 kinase phosphorylation, an inhibitor of ERK-1 and ERK-2 kinase phosphorylation, or a combination thereof. In other additional embodiments, the second active agent is an inhibitor of a mutant EGFR kinase, or tyrosine-protein kinase.

In yet other embodiments, the second active agent is osimertinib, gefitinib, erlotinib, afatinib, or a combination thereof. In various other embodiments, the second active agent is an inhibitor of a fusion kinase, wherein the fusion kinase is EML4-ALK or Bcr-Abl. In yet other various embodiments, the fusion kinase is EML4-ALK and the second active agent is ceritinib, crizotinib, alectinib, brigatinib, or a combination thereof. In various additional embodiments, the fusion kinase is Bcr-Abl and the second active agent is imatinib, dasatinib, nilotinib, bosutinib, ponatinib, or a combination thereof.

This disclosure also provides various embodiments wherein a) the carrier comprises water, a buffer, a sugar, a cellulose, a cyclodextrin, dimethyl sulfoxide, polyethylene glycol, tocopherol, a liposome, a micelle, or a combination thereof, or b) the excipient comprises, a binder, a lubricant, a sorbent, a vehicle, a disintegrant, a preservative, or a combination thereof.

In various other embodiments, the concentration of PAC-1 is about 0.1 µM to about 50 µM. In additional embodiments, the concentration of PAC-1 is about 0.1 µM to about 5 µM, about 1 µM to about 10 µM, about 2 µM to about 15 µM, about 3 µM to about 20 µM, about 4 µM to about 25 µM, about 5 µM to about 30 µM, about 10 µM to about 40 µM, about 15 µM to about 50 µM, about 20 µM to about 75 µM, about 25 µM to about 100 µM, about 50 µM to about 100 µM, or about 0.1 nM to about 5 µM.

In further embodiments, the concentration of the second active agent is about 1 nM to about 100 µM. In some additional embodiments, the concentration of the second active agent is about 0.1 nM to about 100 µM, about 0.5 nM to about 0.5 µM, about 0.5 nM to about 1 µM, about 1 nM to about 10 µM, about 1 nM to about 20 µM, about 10 nM to about 50 µM, about 0.1 µM to about 10 µM, about 0.1 µM to about 20 µM, about 1 µM to about 30 µM, about 10 µM to about 50 µM, about 10 µM to about 75 µM, or about 15 µM to about 100 µM.

This disclosure provides various embodiments of a method of inhibiting the growth or proliferation of cancer cells comprising contacting cancer cells with an effective amount of a composition of any one of the disclosed compositions, thereby inhibiting the growth or proliferation of the cancer cells. There are also various embodiments of a method of inducing apoptosis in a cancer cell comprising contacting the cancer cell with an effective amount of a composition of any one of the disclosed compositions, wherein apoptosis is thereby induced in the cancer cell.

Disclosed herein are various embodiments of a method of treating a cancer comprising administering to a patient in need thereof, concurrently or sequentially, a therapeutically effective amount of the compound PAC-1, and an effective amount of a second active agent, wherein the second active agent is an inhibitor of a mutant kinase or an inhibitor of a fusion kinase; wherein the cancer is thereby treated.

In a variety of embodiments, the second active agent is an inhibitor of a mutant EGFR kinase, an inhibitor of mutant c-kit, an inhibitor of EML4-ALK fusion kinase, or an inhibitor of Bcr-Abl fusion kinase, wherein the mutant EGFR kinase optionally has the T790M mutation. In other embodiments, a pro-apoptotic Bcl-2 protein (BIM) is upregulated.

In additional embodiments, a cancer is treated by degrading or abolishing both MEK-1 and MEK-2 kinases, thereby effectively inhibiting the MAPK signaling pathway and inducing apoptosis in a cancer cell, by inhibiting phosphorylation of MEK-1 and MEK-2, ERK-1 and ERK-2, or a combination thereof. In other additional embodiments of this disclosure, the cancer is melanoma, leukemia, gastric cancer, kidney cancer, lung cancer, brain cancer, or metastatic forms thereof. In yet other embodiments of this disclosure, the second active agent is osimertinib, gefitinib, erlotinib, afatinib, ceritinib, crizotinib, alectinib, brigatinib, dasatinib, nilotinib, bosutinib, ponatinib, trametinib, cobimetinib, binimetinib, or imatinib, wherein resistance to treatment of a cancer in a patient in need thereof is reduced, delayed, or eliminated.

In various additional embodiments, PAC-1 synergizes with osimertinib, ceritinib, or imatinib in vitro or in vivo, wherein:

a) the concentration of PAC-1 is about 2 µM to about 5 µM, the second active agent is osimertinib, and the concentration of osimertinib is about 1 nM to about 30 nM;

b) the concentration of PAC-1 is about 2 µM to about 5 µM, the second active agent is ceritinib, and the concentration of ceritinib is about 5 nM to about 30 nM; or c) the concentration of PAC-1 is about 5 µM to about 7.5 µM, the second active agent is imatinib, and the concentration of imatinib is about 60 nM to about 100 nM.

In various embodiments, as would be readily recognized by one of skill in the art, the concentrations of PAC-1 and the second active agent(s) recited throughout this disclosure can also be recited and interpreted as ratios of PAC-1 to the second active agent, for example, by converting the concentrations recited herein to their corresponding molar ratios of PAC-1 to the second active agent(s).

In a variety of other embodiments, the compound PAC-1 and the second active agent are concurrently administered to a cancer patient. In yet other embodiments, the compound PAC-1 and the second active agent are sequentially administered to a cancer patient. In some more embodiments, the compound PAC-1 is administered to a cancer patient before the second active agent. In even more embodiments, the compound PAC-1 is administered to a cancer patient after the second active agent.

In various additional embodiments, the methods further comprise administering to the patient, concurrently or sequentially, a therapeutically effective amount of a MEK inhibitor, a V600E mutated BRAF kinase inhibitor, or a combination thereof. In yet more embodiments, the MEK inhibitor is trametinib, cobimetinib, binimetinib, or a combination thereof. In additional embodiments, the mutated BRAF kinase inhibitor is vemurafenib, dabrafenib, encorafenib, or a combination thereof.

In this disclosure, there are various embodiments for the use of a composition to prepare a medicament for the treatment of cancer, the composition comprising:

(a) the compound PAC-1;

(b) at least one second active agent, wherein the second active agent is an inhibitor of a mutant kinase or an inhibitor of a fusion kinase; and (c) optionally a pharmaceutically acceptable diluent, excipient, carrier, or combination thereof;

wherein the composition is an enhancer of MEK kinase degradation.

In various embodiments throughout the disclosure, the cancer is melanoma, leukemia, gastric cancer, kidney cancer, lung cancer, brain cancer, or metastatic forms thereof.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

Results

Figure 1:
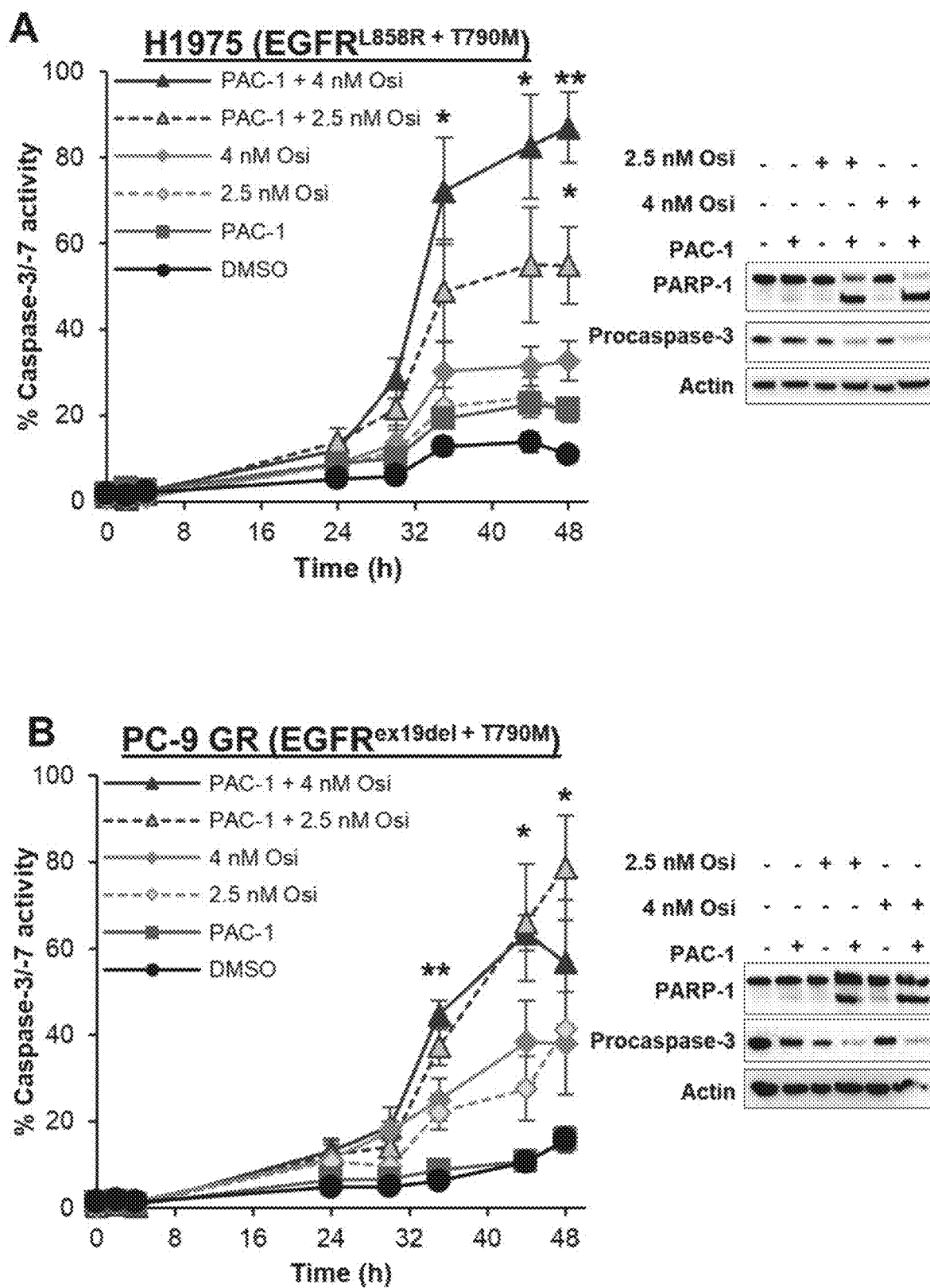
FIG. 1. Enhancement of caspase-3 activity following co-treatment of cancer cells with PAC-1 and diverse targeted kinase inhibitors. Negligible increases in caspase-3 activity or PARP-1 cleavage was observed in (A) H1975 and (B) PC-9 GR NSCLC cells treated with DMSO, single-agent PAC-1 (5 μM) or osimertinib. In cells treated with PAC-1+ osimertinib, dramatic increases in caspase-3 activity was observed as early as 36 h post-treatment. Significant PARP-1 cleavage and reduction in procaspase-3 levels were observed after 48 h, consistent with results obtained from the caspase-3 activity assay. (C) H3122 NSCLC cells were treated with PAC-1 (5 μM)+ceritinib for varying periods of time and a significant increase in caspase-3 activity is observed. Increased PARP-1 cleavage and reduction in procaspase-3 levels were also observed after a 48 h treatment. (D) Significant enhancement of caspase-3 activity was also observed in K-562 cells treated with PAC-1 (7.5 μM)+ imatinib with negligible single-agent activity. Following 48 h of PAC-1+imatinib treatment, increased PARP-1 cleavage and procaspase-3 activation were also observed. Values shown are averages of at least 3 experiments, error bars are s.e.m., p values shown for two-way ANOVA analysis to determine if the combination is different from an additive effect of individual agents are statistically different (* $p<0.05$,  $p<0.01$, * $p<0.001$). See also FIG. 6.
Figure 1:
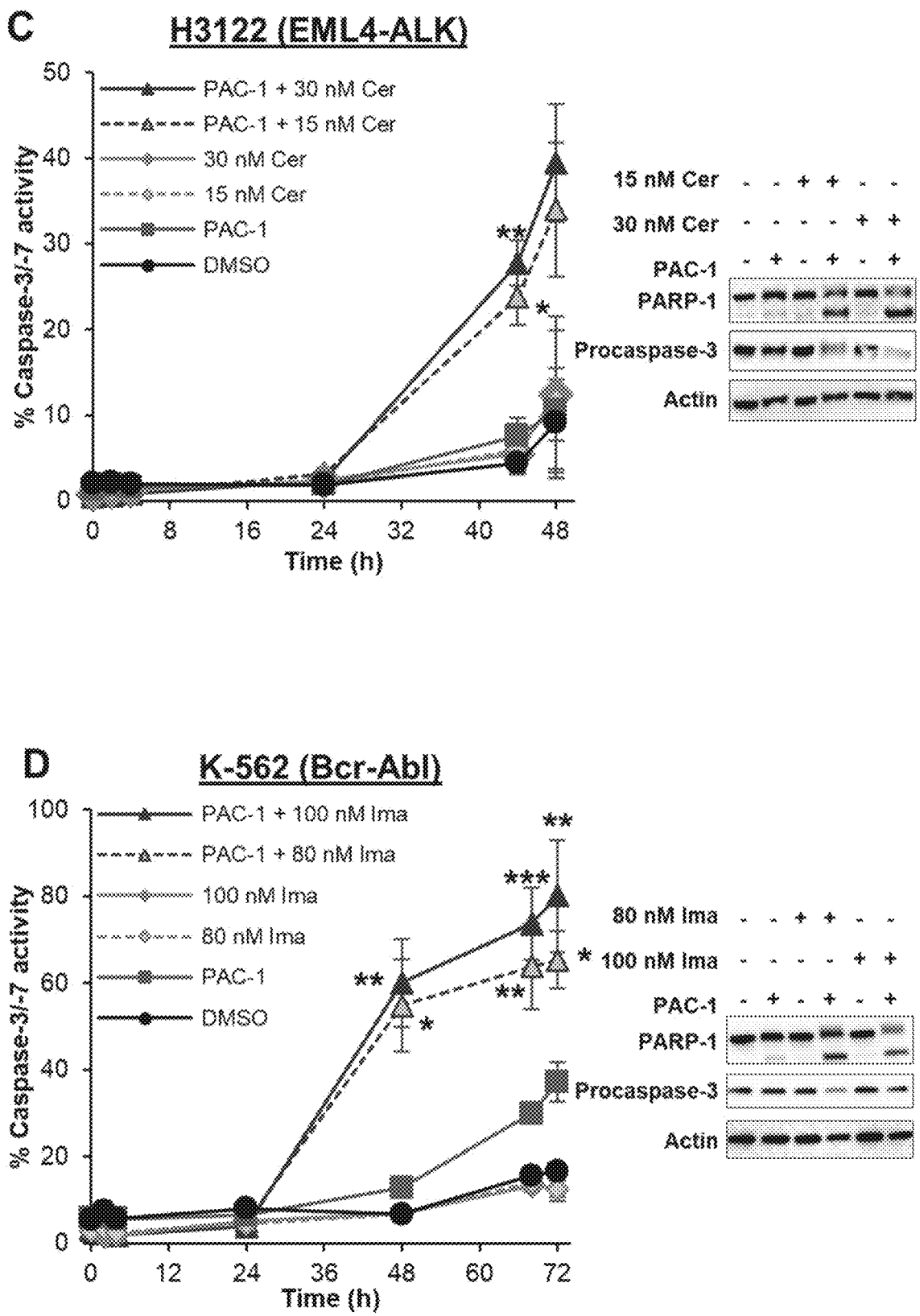
Figure 6:
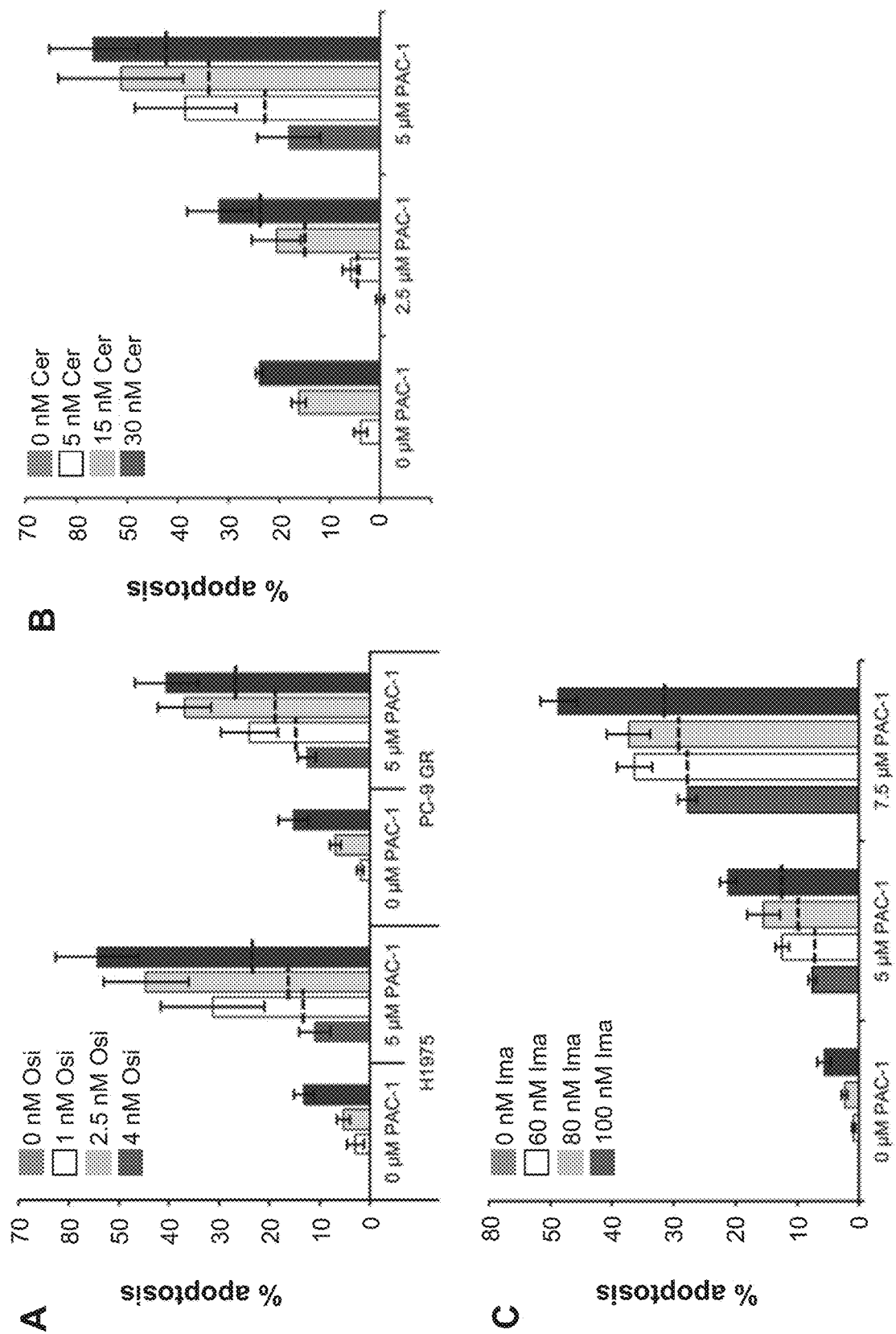
FIG. 6. Enhanced apoptotic cell death in cells treated with PAC-1 and clinically approved targeted kinase inhibitors. Related to FIG. 1. (A) $EGFR^{T790M}$ cells and (B) H3122 cells were treated with indicated concentrations of PAC-1+osimertinib or PAC-1+ceritinib, respectively for 48 hours. (C) K-562 cells were treated with indicated concentrations of PAC-1+imatinib for 72 hours. Cells were then stained with Annexin V-FITC and PI dyes and analyzed via flow cytometry. Data shown is average of at least three independent experiments and error bars are s.e.m. The dashed horizontal lines on the bar graphs represent the level of apoptotic cell death expected from an additive effect of the compounds.

Caspase-3 Activity is Significantly Enhanced in Cells Treated with PAC-1 and Diverse Kinase Inhibitors As shown in FIGS. 1A and 1B, PAC-1 significantly increases the caspase-3 activity in osimertinib-treated non-small cell lung cancer (NSCLC) cell lines H1975 ($EGFR^{L858R+T790M}$) and PC-9 GR ($EGFR^{ex19del+T790M}$). Increased PARP-1 cleavage and disappearance of the procaspase-3 band were also observed in both cell lines when treated with the combination (FIGS. 1A and 1B). A similar effect is also observed in H3122 NSCLC cells (harboring the EML4-ALK fusion) co-treated with PAC-1 and ceritinib (FIG. 1C) and K-562 chronic myelogenous leukemia (CML) cells (harboring the BCR-ABL fusion) treated with PAC-1 and imatinib (FIG. 1D). The enhancement of caspase-3 activity observed at longer timepoints (FIG. 1) was determined to be synergistic using a two-way ANOVA test. As a result of increased caspase-3 activity, a significantly larger population of cells treated with the combination of PAC-1 and osimertinib/ceritinib/imatinib die via apoptosis (FIGS. 6A-C). Collectively these results demonstrate that, in addition to general cytotoxins and inhibitors against $BRAF^{V600E}$, PAC-1 is able to broadly enhance the caspase-3 activity of kinase inhibitors targeted to $EGFR^{T790M}$, EML4-ALK, and BCR-ABL.

Caspase-3 Activity Leads to Degradation of MEK Kinases

Activation of an executioner caspase such as caspase-3 leads to the cleavage of hundreds of proteins in the cell. Intriguingly, the protein substrates for caspase-3 tend to be found in protein complexes or signaling pathways that govern cell fate and survival. Proteome-wide identification of caspase-3 substrates by the Wells (Mahrus, et al., Cell 2008, 134, 866) and Cravatt (Dix, et al., Cell 2008, 134, 679) laboratories have independently shown that both MEK1 and MEK2 kinases are cleaved during caspase-3-mediated apoptosis. Moreover, it has also been previously shown that MEK1 and MEK2 are the only kinases that phosphorylate ERK1/2, serving as the critical gatekeepers of ERK1/2 activity. Given the observation that addition of PAC-1 to diverse kinase inhibitors leads to enhanced apoptosis, a hypothesis was formulated that the dramatic increase in caspase-3 activity leads to MEK1 and MEK2 degradation, inhibiting downstream pro-survival signaling.

Figure 2:
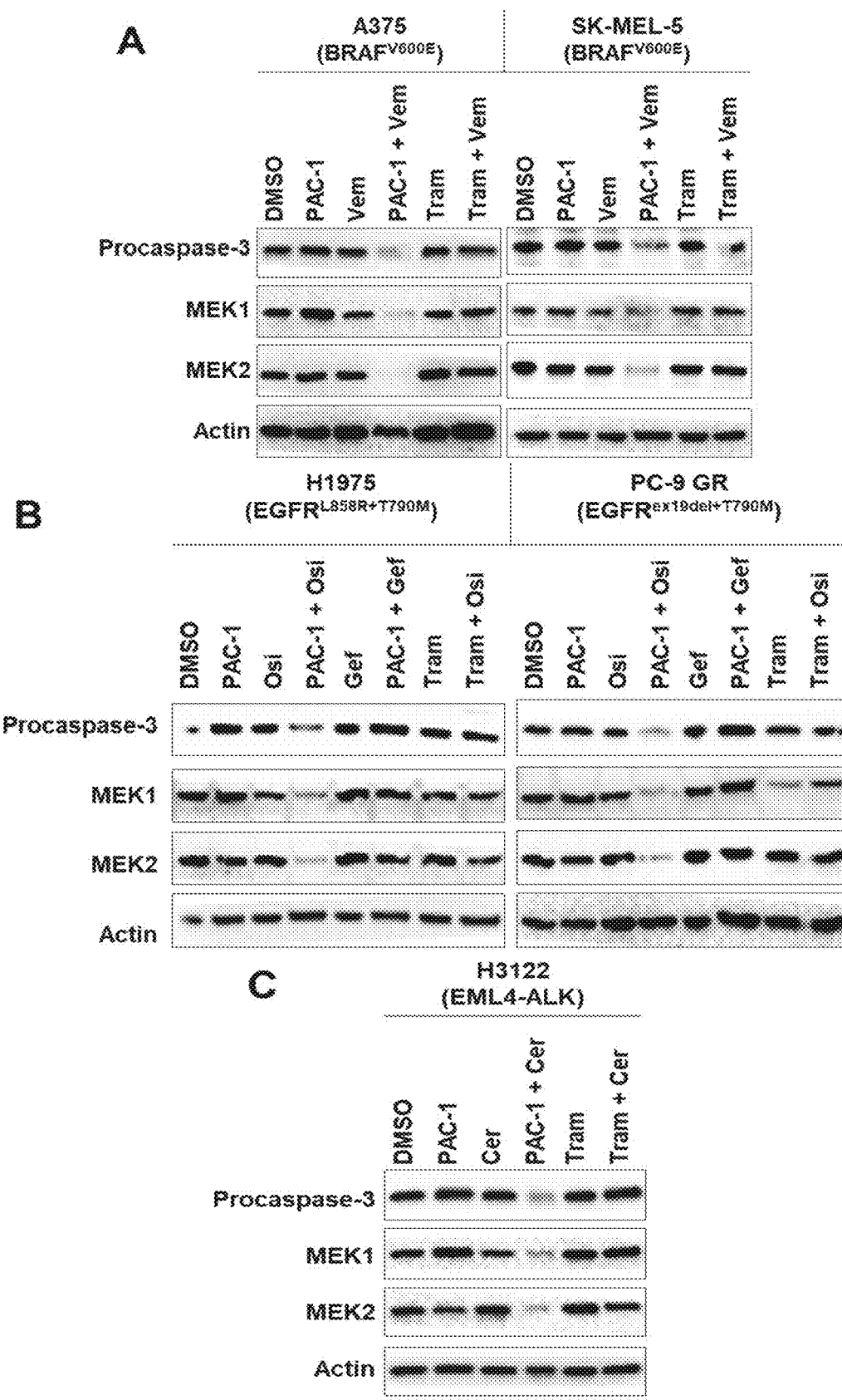
FIG. 2. PAC-1 combination therapies lead to caspase-3 activation and degradation of MEK1 and MEK2 kinases. (A) Procaspase-3 activation leads to dramatic reduction in MEK1 and MEK2 levels in A375 and SK-MEL-5 cells treated with PAC-1 (5 μM)+vemurafenib (10 μM) for 48 hours. This reduction was not observed in cells treated with trametinib (30 nM)+vemurafenib. (B) H1975 and PC-9 GR cells treated with PAC-1 (5 μM)+osimertinib (4 nM) for 48 hours led to procaspase-3 activation and corresponding degradation of MEK1 and MEK2 kinases. This was not observed in cells treated with PAC-1+gefitinib (4 nM) or trametinib (30 nM)+osimertinib. (C) MEK1 and MEK2 degradation were similarly observed in H3122 cells treated with PAC-1 (5 μM)+ceritinib (30 nM) for 48 hours but not in cells treated with trametinib (30 nM)+ceritinib. See also FIG. 7 and FIG. 8.

To investigate this hypothesis, levels of MEK1 and MEK2 kinases in $BRAF^{V600E}$ cell lines were probed following treatment with PAC-1+vemurafenib or trametinib+vemurafenib. In both A375 and SK-MEL-5 cells treated with PAC-1+vemurafenib for 48 h, dramatic reduction in procaspase-3, MEK1, and MEK2 levels were observed, suggesting that procaspase-3 activation led to MEK1 and MEK2 degradation (FIG. 2A). In contrast, when these two cell lines are treated with trametinib and vemurafenib, no observable change in the levels of procaspase-3, MEK1, and MEK2 was detected (FIG. 2A). It is worth noting that MEK1/2 cleavage products are transiently stable (Dix et al., 2008), making their detection after a 48 hour treatment challenging.

Figure 7:
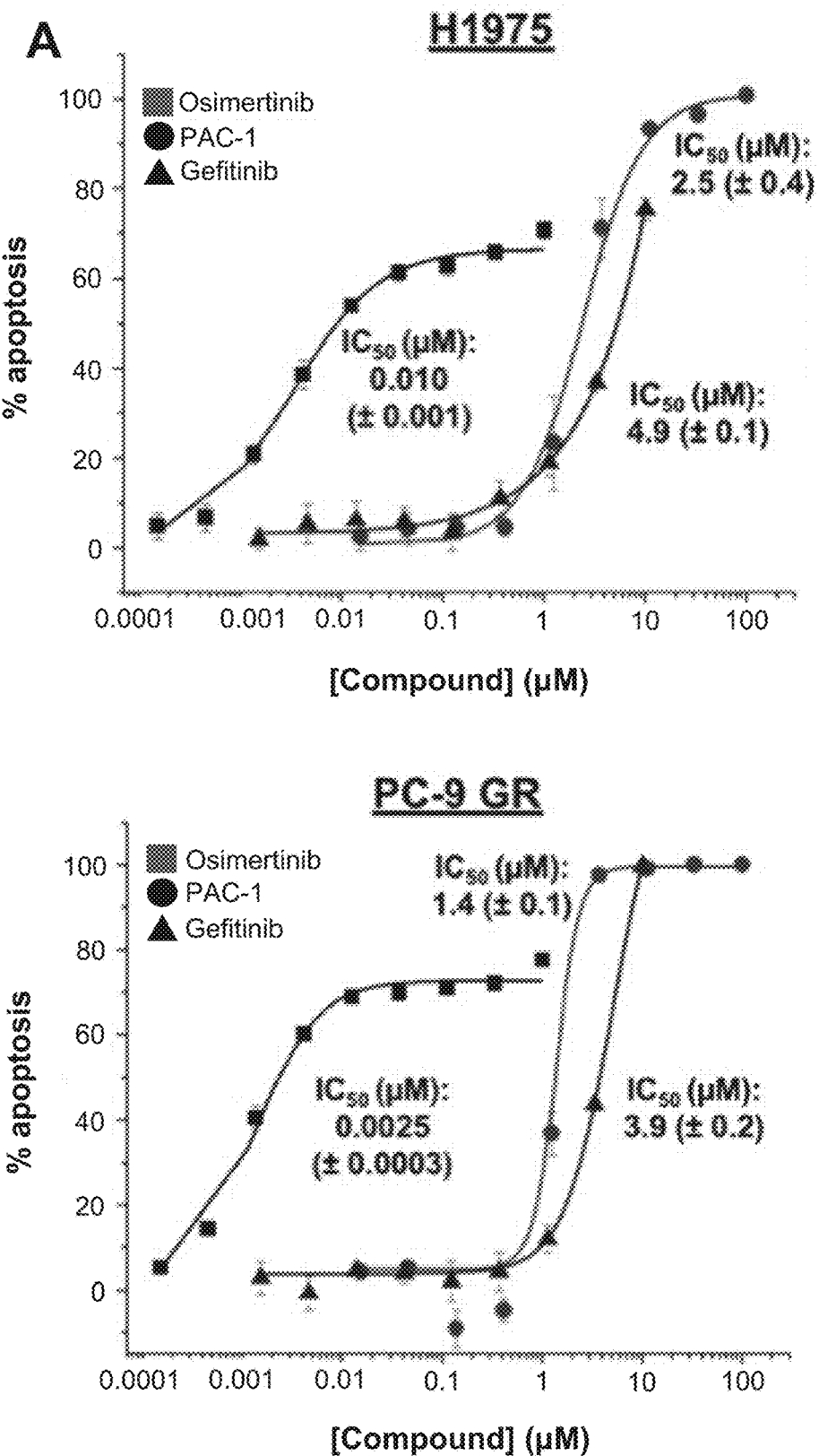
FIG. 7. MEK1/2 degradation observed with lower concentrations. Related to FIG. 2. (A) $IC_{50}$ values (±s.e.m) of PAC-1, osimertinib, and gefitinib in PC-9 GR and H1975 cells following a 5-day incubation. Data shown is average of at least three independent experiments. (B-C) Degradation of MEK1/2 kinases in cells treated with lower concentrations of PAC-1+osimertinib or PAC-1+ceritinib for 48 hours. (D) Treatment of K-562 (BCR-ABL) cells with imatinib in combination with either PAC-1 or trametinib for 48 hours led to procaspase-3 activation and MEK1/2 degradation. (E) After 48 hours, lower concentration of imatinib (80 nM) in combination with PAC-1 also led to procaspase-3 and resultant degradation of MEK1/2 kinases.
Figure 7:
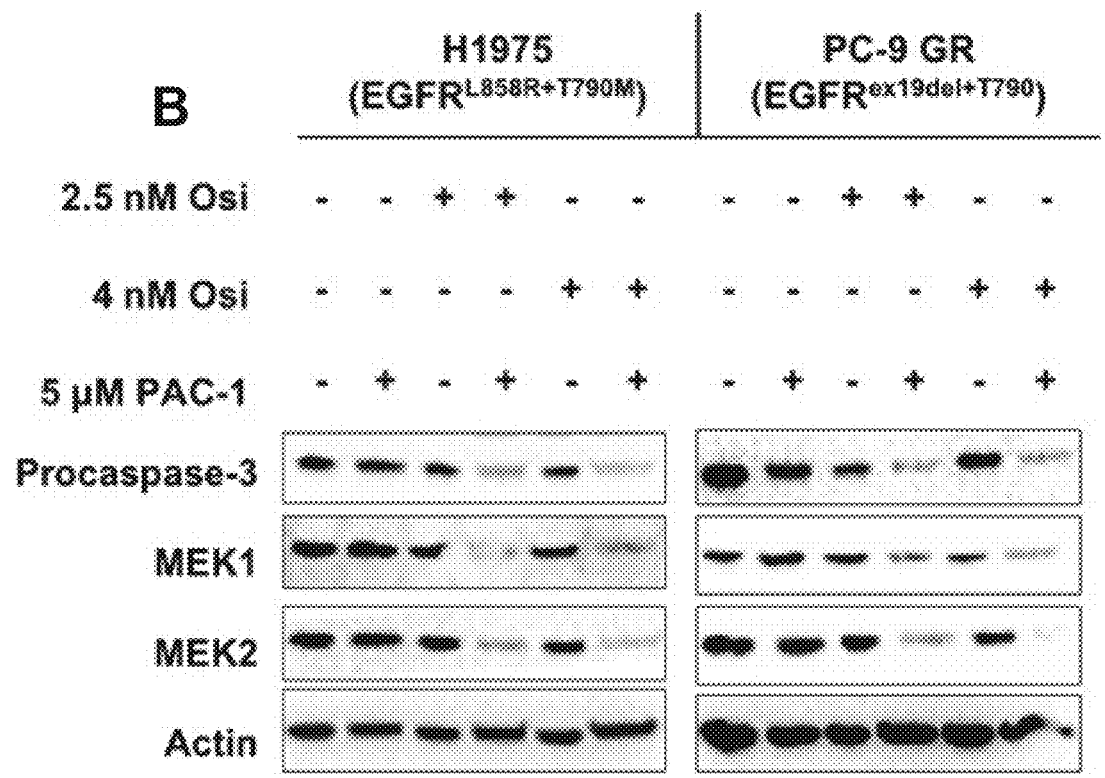
Figure 7:
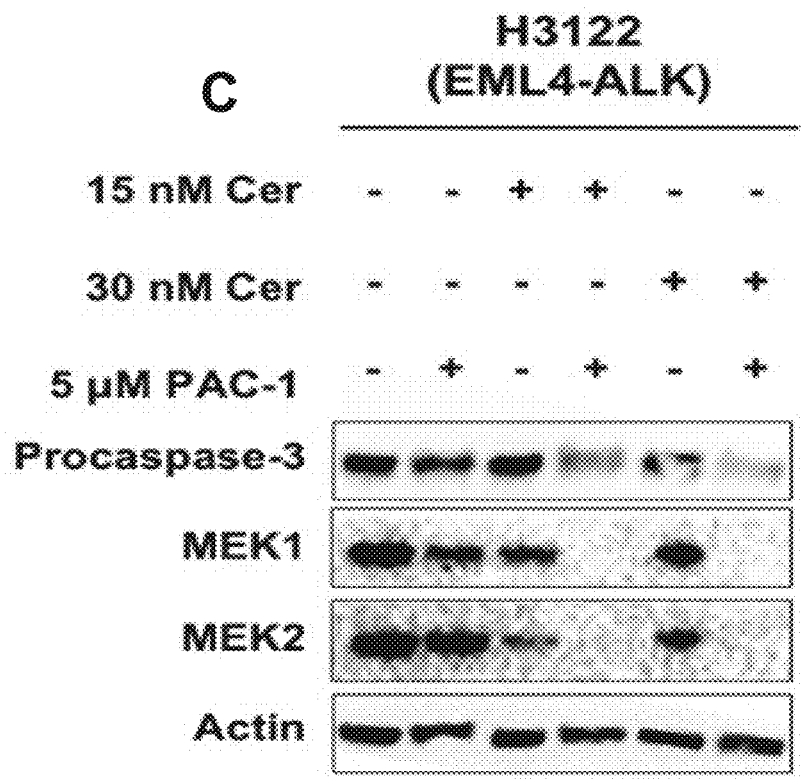
Figure 7:
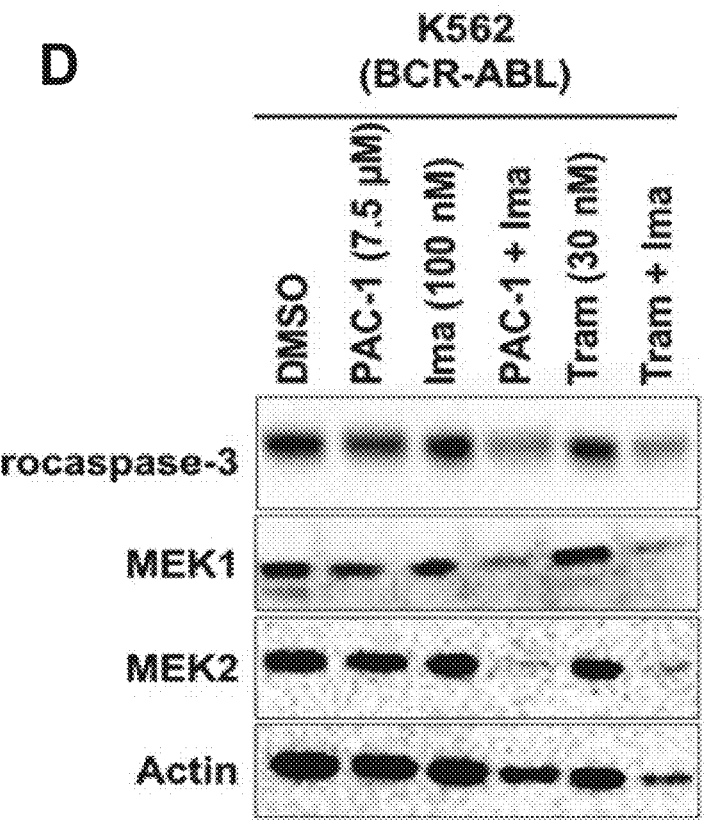
Figure 7:
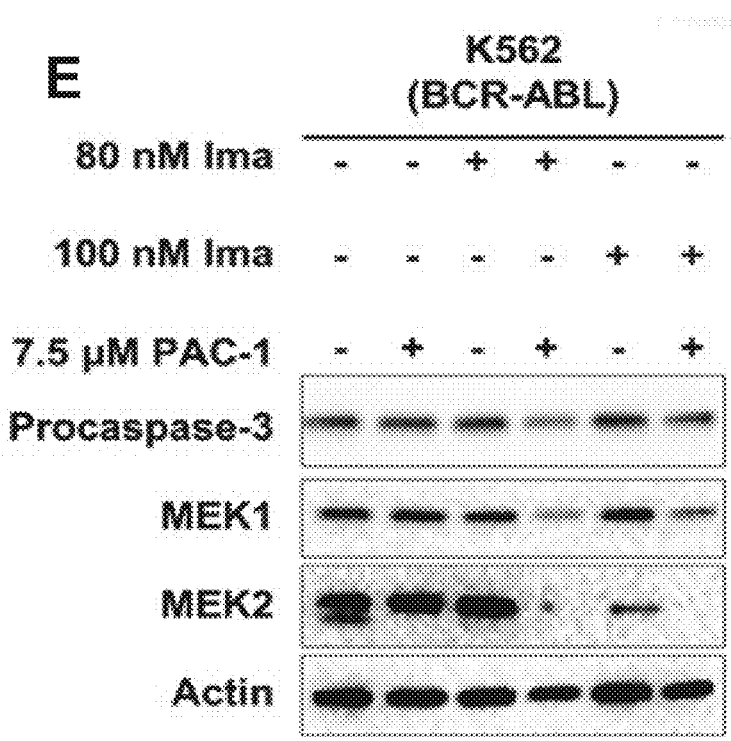

To investigate the generality of these results, changes in procaspase-3, MEK1, and MEK2 levels in $EGFR^{T790M}$, EML4-ALK, and BCR-ABL cells were assessed following combination treatment with PAC-1 and kinase inhibitors specific for those alterations. In both H1975 and PC-9 GR cells, treatment with PAC-1 and osimertinib (4 nM) led to dramatic reduction in procaspase-3, MEK1, and MEK2 levels, but not when the inactive inhibitor gefitinib (FIG. 7A) was used (FIG. 2B). Using a lower concentration of osimertinib (2.5 nM) also led to degradation of MEK1 and MEK2 kinases (FIG. 7B). Importantly, co-treatment with trametinib and osimertinib did not lead to reduction in MEK1 and MEK2 levels in either cell lines (FIG. 2B), similar to that observed in $BRAF^{V600E}$ cell lines. Degradation of MEK1 and MEK2 was also seen in H3122 cells when they were co-treated with PAC-1+ceritinib (FIG. 2C), even when at reduced concentrations of ceritinib (FIG. 7C). Co-treatment with trametinib and ceritinib did not lead to reduction in MEK1 and MEK2 levels in H3122 cells (FIG. 2C), consistent with data obtained in $BRAF^{V600E}$ and $EGFR^{T790M}$ cells. Extensive procaspase-3 activation was observed in K-562 cells treated with either PAC-1+imatinib or trametinib+imatinib, and degradation of MEK1 and MEK2 kinases was also observed in both samples (FIG. 7D). Varying the concentration of imatinib used also led reduction in MEK1 and MEK2 levels (FIG. 7E).

Figure 8:
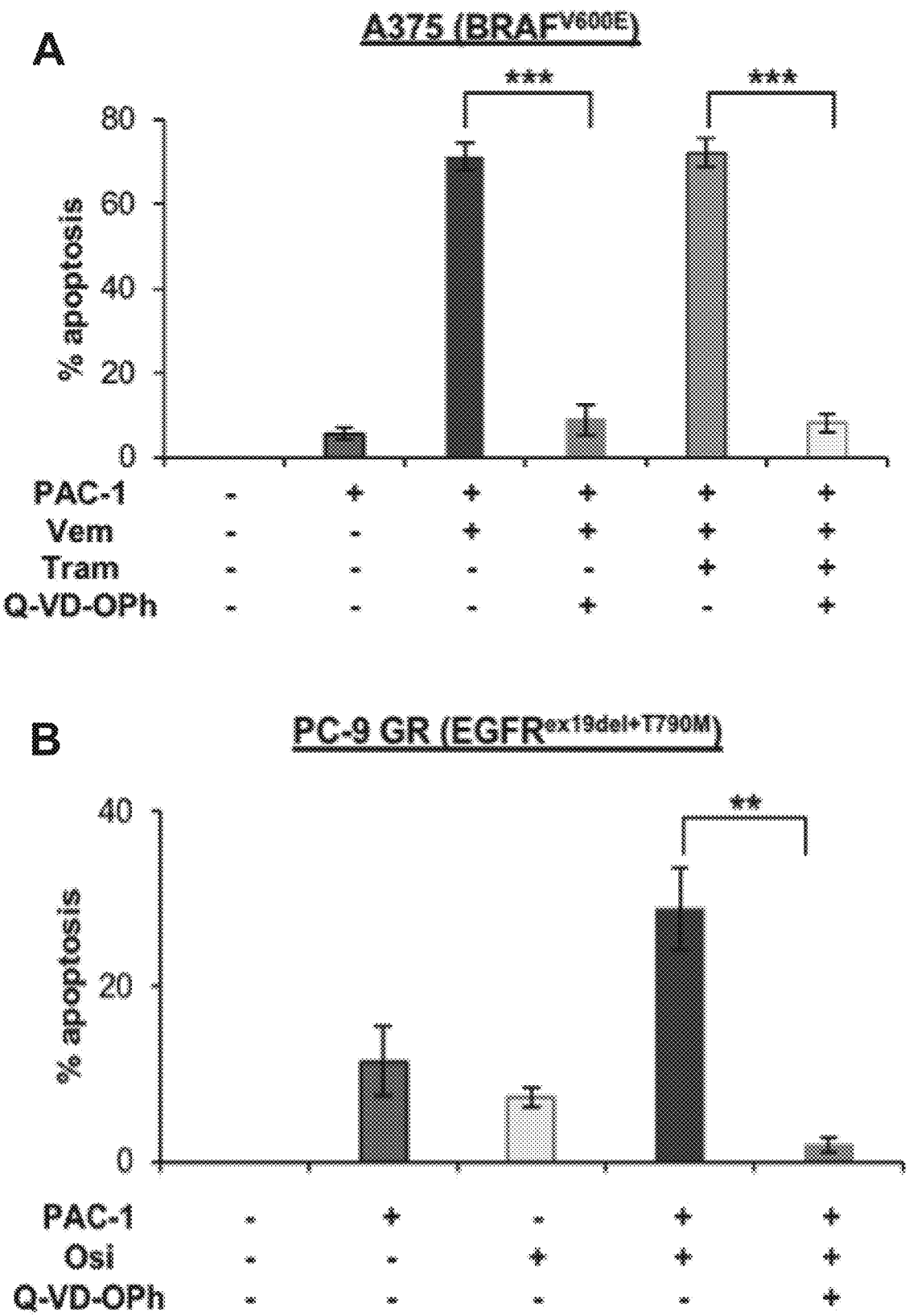
FIG. 8. Protection from cell death in cells treated with PAC-1+targeted kinase inhibitors using caspase inhibitor Q-VD-OPh (25 μM) for 48 hours. Related to FIG. 2. (A) A375 cells treated with PAC-1 (5 μM), vemurafenib (10 μM), trametinib (30 nM), Q-VD-OPh, and combinations thereof. (B) PC-9 GR cells were treated PAC-1 (5 μM), osimertinib (4 nM), Q-VD-OPh, and combinations thereof (C) H3122 cells were treated PAC-1 (5 μM), ceritinib (30 nM), Q-VD-OPh, and combinations thereof. (D) K-562 cells treated with PAC-1 (7.5 μM), imatinib (100 nM), Q-VD-OPh, and combinations thereof. Cells were stained with Annexin V-FITC and PI dyes and analyzed via flow cytometry. Data shown is average of at least three independent experiments and error bars are s.e.m. p-values shown for two-way t-test;  $p\leq0.01$, * $p\leq0.001$. (E-G) MEK1/2 cleavage is attenuated in cells treated with PAC-1+targeted kinase inhibitors+caspase inhibitor Q-VD-OPh. (E) A375 cells treated with PAC-1 (5 μM), vemurafenib (10 μM), Q-VD-OPh (25 μM), and combinations for 48 hours. (F) PC-9 GR cells were treated PAC-1 (5 μM), osimertinib (4 nM), Q-VD-OPh (25 µM), and combinations for 48 hours. (G) H3122 cells were treated PAC-1 (5 µM), ceritinib (30 nM), Q-VD-OPh (25 µM), and combinations for 48 hours.
Figure 8:
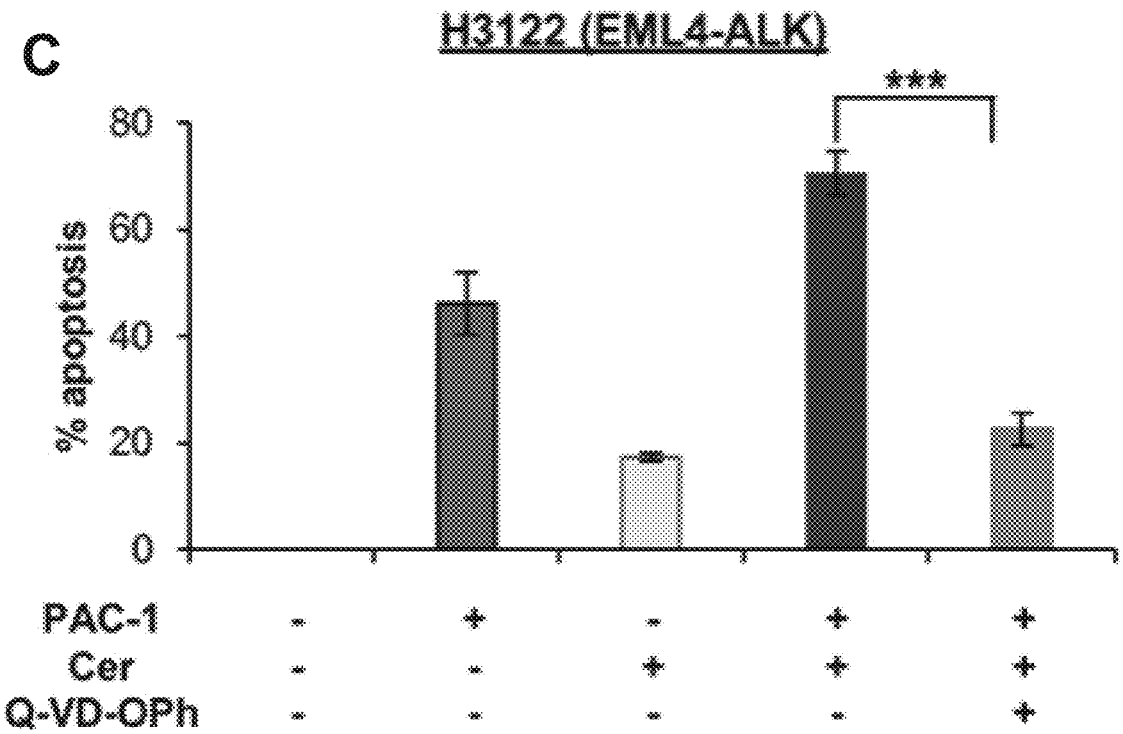
Figure 8:
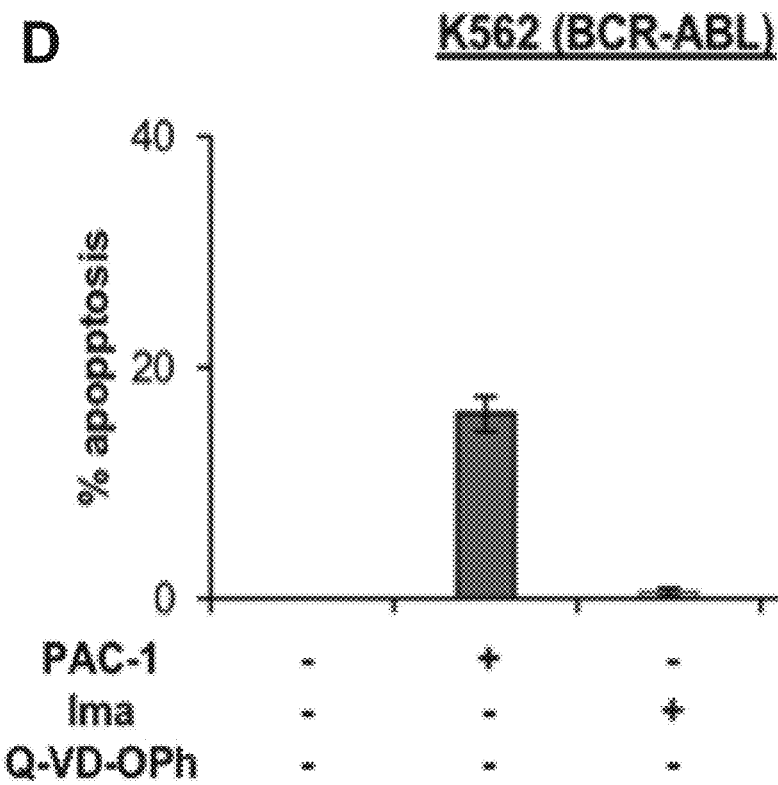
Figure 8:
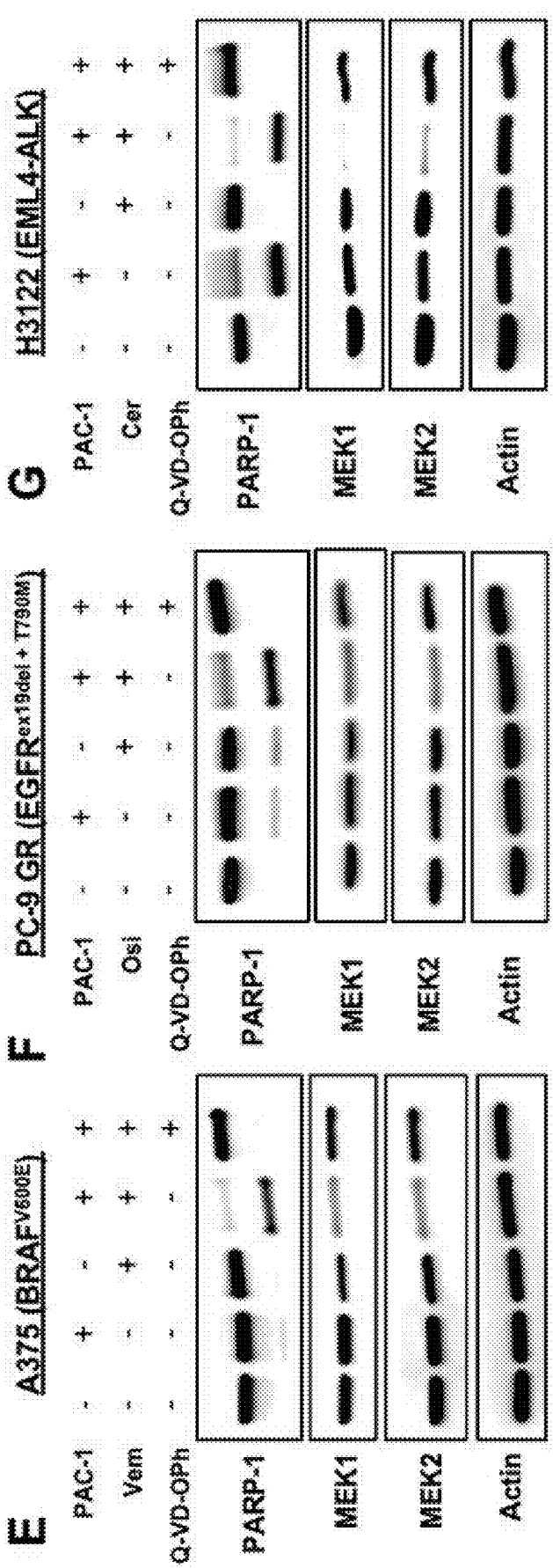

To provide further mechanistic understanding on the importance of caspase-3 activity in mediating the synergistic cell death observed in the PAC-1/drug combination, Q-VD-OPh, a general caspase inhibitor, was used. In these experiments, protection of apoptotic cell death (FIGS. 8A-D) as well as attenuated MEK1/2 cleavage (FIGS. 8E-G) were both observed when Q-VD-OPh was added concurrently to cells treated with PAC-1/drug combinations. These results suggest that inhibition of caspase-3 activity, in particular, its activity in cleaving MEK1 and MEK2 kinases, was sufficient to abolish the dramatic synergy observed in cells treated with the PAC-1/drug combinations. Taken together, the disclosed results indicate the importance of caspase-3-induced MEK1/2 cleavage in mediating the synergistic apoptotic cell death, and the generality of this observation in diverse cancer types.

Degradation of MEK1 and MEK2 Kinases Leads to Sustained Inhibition of MEK1/2 and ERK1/2 Phosphorylation Significant inhibition (>80%) of ERK1/2 phosphorylation is necessary for the clinical efficacy of targeted kinase inhibitors like vemurafenib. Since reactivation of ERK1/2 phosphorylation is commonly observed in resistant tumors, a MEK1/2 inhibitor has been added to the treatment regimen to achieve sustained ERK1/2 inhibition. While clinically approved MEK1/2 inhibitors are effective in preventing ERK1/2 phosphorylation, the inhibition of ERK1/2 activity disrupts the negative feedback on RAF, resulting in RAF hyper-activation and hyper-phosphorylation of MEK1/2. The rebound in MEK1/2 phosphorylation subsequently leads to pathway reactivation. Development of "feedback buster" MEK1/2 inhibitors such as trametinib is intended to mitigate the rebound but that effect is transient. Therefore, sustained inhibition of both MEK1/2 and ERK1/2 remains challenging despite the availability of numerous MEK1/2 inhibitors.

Given that enhanced caspase-3 activity led to degradation of MEK1/2 kinases, a hypothesis was formulated that PAC-1 combination therapies would lead to sustained inhibition of MEK1/2 and ERK1/2 phosphorylation. Addition of PAC-1 to vemurafenib led to inhibition of ERK1/2 phosphorylation in both A375 (FIGS. 3A and 3B) and SK-MEL-5 cells (FIG. 3A), consistent with previous work. While sustained inhibition of MEK1/2 phosphorylation was observed when cells were treated with vemurafenib+PAC-1 due to the degradation of MEK1 and MEK2 kinases, a dramatic rebound in MEK1/2 phosphorylation was rapidly seen in trametinib+vemurafenib treated cells (FIG. 3B). This observation is consistent with a previous report detailing the transient (6 h) effect of trametinib in inhibiting MEK1/2 phosphorylation in mutant BRAF melanoma cells. These results suggest the distinct advantage of drug-induced degradation of MEK1 and MEK2 kinases as an effective strategy to inhibit both MEK1/2 and ERK1/2 activity.

To explore the generality of this effect, H1975 and PC-9 GR cells were treated with PAC-1 and osimertinib and probed for changes ERK1/2 and MEK1/2 phosphorylation. As seen in FIGS. 3C and 3D, $EGFR^{T790M}$ cells treated with PAC-1 and osimertinib led to sustained loss of ERK1/2 and MEK1/2 phosphorylation, as a result of MEK1 and MEK2 degradation. Using PAC-1 and gefitinib, no corresponding reduction in ERK1/2 or MEK1/2 phosphorylation is observed (FIG. 3C), indicating that the effect with osimertinib is specific for the $EGFR^{T790M}$ target. At a lower concentration of osimertinib, sustained inhibition of MEK1/2 and ERK1/2 phosphorylation (FIG. 9A) corresponding to degradation of MEK1 and MEK2 kinases was also observed (FIG. 7B). Rapid rebound of MEK1/2 phosphorylation similarly occurs within 24 hour of treatment with osimertinib and trametinib but not in cells treated with osimertinib and PAC-1 (FIG. 3D), mirroring the effect seen in $BRAF^{V600E}$ cells.

In a similar fashion, H3122 cells (EML4-ALK) were treated with PAC-1+ceritinib or trametinib+ceritinib and probed for changes in ERK1/2 and MEK1/2 phosphorylation. In this case, H3122 cells co-treated with PAC-1+ceritinib for 48 hours also led to sustained reduction in ERK1/2 and MEK1/2 phosphorylation (FIG. 9B and FIG. 9D), which can be attributed to the caspase-3-mediated degradation of MEK1 and MEK2 kinases. When used in combination with PAC-1, even lower concentration of ceritinib cause sustained inhibition of MEK1/2 and ERK1/2 phosphorylation (FIG. 9C), due to degradation of MEK1 and MEK2 kinases (FIG. 7C). Similarly, transient inhibition of MEK1/2 phosphorylation was also observed in H3122 cells treated with trametinib and ceritinib (FIG. 9D), consistent with results seen in $BRAF^{V600E}$ and $EGFR^{T790M}$ cells.

Finally, in K-562 cells expressing BCR-ABL, co-treatment with PAC-1 and imatinib also lead to sustained inhibition of ERK1/2 and MEK1/2 phosphorylation (FIG. 9E) due to extensive degradation of MEK1 and MEK2 kinases (FIG. 7D). It should be noted that rebound of MEK1/2 phosphorylation was not observed in cells treated with trametinib+imatinib for 48 hours (FIG. 9E), since degradation of MEK1 and MEK2 kinases was also observed in this cell line (FIG. 7D). Similarly, varying the concentration of imatinib used also led reduction in phospho-MEK1/2 and phospho-ERK1/2 levels (FIG. 9F) due to degradation of MEK1 and MEK2 (FIG. 7E). Collectively, the disclosed results demonstrate the ability of PAC-1, in combination with diverse kinase inhibitors, to provide sustained inhibition of ERK1/2 and MEK1/2 phosphorylation, a result generally not observed in the combinations of these targeted kinase inhibitors with the MEK1/2 inhibitor trametinib.

PAC-1+Vemurafenib is More Efficacious Than Trametinib+Vemurafenib in Eliminating Acquired Resistance Knowing that secondary activating mutations on MEK kinases are commonly found in melanomas resistant to BRAFi+MEKi, a hypothesis was formulated that PAC-1+vemurafenib would be more efficacious than trametinib+vemurafenib in delaying resistance in A375 cells. The rationale behind the hypothesis is that PAC-1+vemurafenib significantly enhances apoptotic cell death leading to degradation of MEK kinases to further inhibit ERK1/2 phosphorylation. To test this hypothesis, A375 cells were treated with PAC-1, vemurafenib, trametinib, and their respective combinations for up to 30 days. Consistent with previous work, resistant colonies were visibly present in A375 cells treated with single-agent vemurafenib as early as 20 days post treatment (FIGS. 4A and 4B). In cells treated with trametinib+vemurafenib, resistant colonies were first noted after 25 days of continuous treatment. Following 30 days of treatment, more resistant colonies were visible in A375 cells treated with trametinib and vemurafenib, indicating the presence of BRAFi+MEKi resistance (FIGS. 4A and 4B). However, emergence of resistant colonies were not observed in A375 cells treated with PAC-1 and vemurafenib in the presence or absence of trametinib following 30 days of treatment (FIGS. 4A and 4B), indicating that the double or triple combination of PAC-1 is significantly more effective in eliminating the onset of vemurafenib resistance as compared to the clinically used BRAFi+MEKi combination.

The Combination of PAC-1 and Osimertinib/Ceritinib is Effective in Eliminating Resistance in $EGFR^{T790M}$ and EML4-ALK Cells The ability of the combination of PAC-1 and osimertinib to delay acquired resistance in $EGFR^{T790M}$ cells was investigated. In this case, H1975 and PC-9 GR cells were treated with indicated concentrations of PAC-1 and/or osimertinib for up to 28 days. In both cell lines, 8 days of single-agent PAC-1 (2 µM) treatment had minimal cytotoxic effect compared to DMSO-treated samples. On the other hand, both single-agent osimertinib (30 nM) and the combination of PAC-1 and osimertinib were very effective inhibiting cell proliferation (FIG. 10). Following 28 days of drug treatment, resistant clones were clearly visible in PC-9 GR and H1975 cells treated only with osimertinib, in contrast to cells treated with both PAC-1 and osimertinib (FIG. 10). These results suggest that the combination of PAC-1 and osimertinib is effective in dramatically delaying or eliminating the onset of osimertinib resistance in $EGFR^{T790M}$ cell lines. Experiments were then conducted to compare the PAC-1+osimertinib combination versus trametinib+osimertinib in delaying resistance in PC-9 GR cells. In this case, PAC-1 or trametinib (5 nM) as single agents had minimal cytotoxic effect as compared to DMSO-treated cells following 8 days of treatment. As expected, treatment with osimertinib, PAC-1+osimertinib, or trametinib+osimertinib for 8 days was effective in inhibiting cell proliferation. Consistent with FIG. 10A, resistant clones were visible in PC-9 GR cells after 28 days of treatment with single-agent osimertinib but not in cells treated with PAC-1 and osimertinib (FIGS. 4C and D). No resistant clones were also visible in cells treated with trametinib and osimertinib after 28 days. While there was a dramatic increase in the number of resistant clones present in cells treated with single-agent osimertinib after 35 days of treatment, no resistant clones were observable in cells treated with either PAC-1+osimertinib or trametinib+osimertinib (FIGS. 4C and D). This observation suggests that the combination of PAC-1+osimertinib is equipotent, but not more efficacious in delaying resistance as trametinib+osimertinib.

Finally, the ability of PAC-1+ceritinib to delay acquired resistance in EML4-ALK cells was investigated. Here, H3122 cells were treated with indicated concentrations of PAC-1, trametinib, ceritinib, or the respective combinations for up to 32 days. Single-agent PAC-1 (2 µM) or trametinib (5 nM) treatment had minimal cytotoxic effect compared to DMSO-treated samples after 8 days of treatment. Treatment with ceritinib, PAC-1+ceritinib, or trametinib+ceritinib for 8 days was effective in inhibiting cell proliferation. (FIG. 4E). Resistant clones were visible in H3122 cells after 20 days of treatment with single-agent ceritinib but not in cells treated with either PAC-1 and osimertinib or trametinib and ceritinib (FIG. 4E). After 32 days of treatment, there was a dramatic increase in the number of resistant clones present in cells treated with single-agent ceritinib but few resistant clones were observable in cells treated with PAC-1+ceritinib (FIG. 4E). In cells treated with trametinib+ceritinib, a number of resistant clones were clearly visible, indicating the presence of ALKi+MEKi resistant H3122 cells (FIGS. 4E and 4F).

Figure 5:
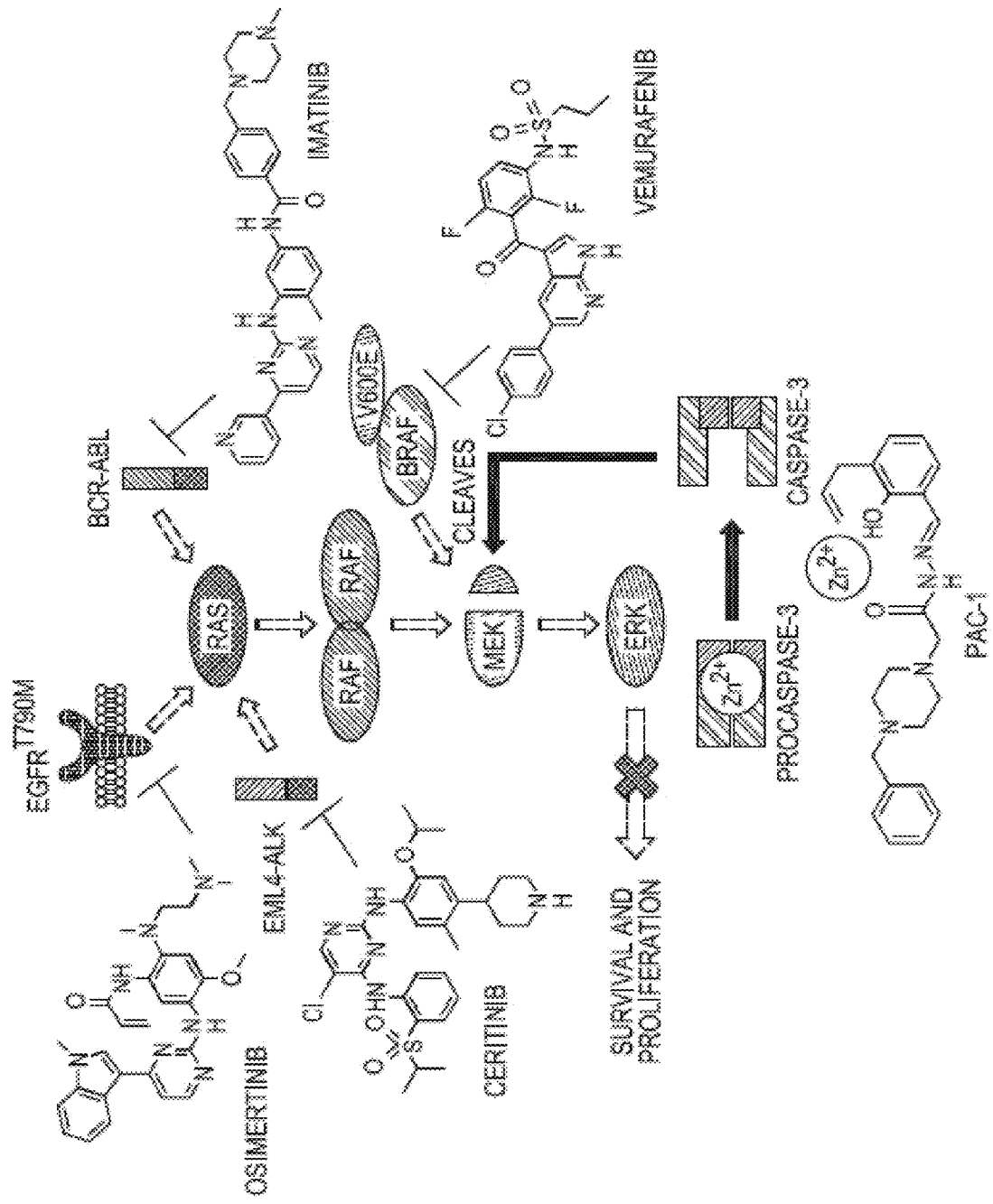
FIG. 5. Proposed mechanism of action of PAC-1 combination therapy with clinically approved kinase inhibitors examined herein. Shown kinase inhibitors target key oncogenic driver kinases, leading to transient inhibition of signaling through MEK. Of critical importance is the ability of PAC-1 treatment to induce cleavage of MEK kinases. This MEK cleavage, in conjunction with upstream pathway inhibition, potently abolishes ERK phosphorylation and hinders pro-survival and proliferation signaling.

In summary, the combination of kinase inhibitors targeting $BRAF^{V600E}$, $EGFR^{T790M}$, EML4-ALK, and BCR-ABL with PAC-1, leads to enhanced procaspase-3 activation and degradation of MEK1 and MEK2 kinases (FIG. 5). The degradation of MEK kinases then leads to sustained inhibition of MEK1/2 and ERK1/2 signaling. The combined effect of increased apoptotic cell death and sustained inhibition of the MAPK pathway that is observed in the PAC-1 combination therapies work in tandem to dramatically delay or eliminate resistance.

Discussion

Significant progress has been made in understanding the mechanisms of acquired resistance to targeted kinase inhibitors. This understanding has translated into combination therapies for $BRAF^{V600E}$ melanomas and next-generation inhibitors for mutant EGFR and fusion EML4-ALK and BCR-ABL kinases. Unfortunately, cancer cells rapidly circumvent inhibition by these next-generation inhibitors via alternative resistance mechanisms, necessitating the development of newer drugs to combat resistant tumors. Moreover, a large proportion of drug-induced resistance remains unexplained, meaning that newer drugs only benefit a small population of patients with molecularly defined resistance mechanisms.

Figure 3:
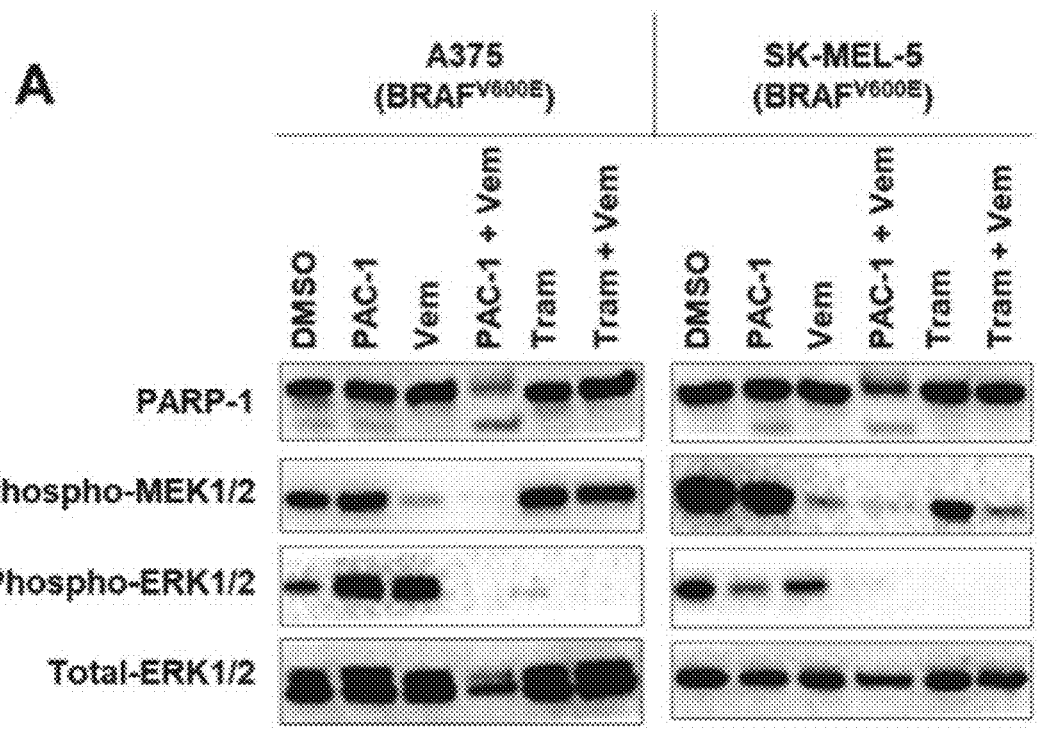
FIG. 3. Cells treated with PAC-1 and vemurafenib or osimertinib have sustained inhibition of MAPK signaling. (A) A375 and SK-MEL-5 melanoma cells were treated with PAC-1 (5 μM), vemurafenib (10 μM), trametinib (30 nM), or the indicated combinations for 48 h. Inhibition of both ERK1/2 and MEK1/2 phosphorylation was only observed in cells treated with PAC-1+vemurafenib. (B) Timecourse of phospho-MEK1/2 and phospho-ERK1/2 inhibition in A375 cells treated with DMSO, vemurafenib, vemurafenib+ PAC-1 or vemurafenib+trametinib for 6, 24, or 48 hours. (C) After 48 hours of treatment with PAC-1 (5 μM)+osimertinib (4 nM), sustained inhibition of both MEK1/2 and ERK1/2 phosphorylation were observed in H1975 and PC-9 GR cells. Treatment with PAC-1+gefitinib (4 nM) for a similar time period did not lead to similar observations. Sustained inhibition of MEK1/2 phosphorylation was also not observed in cells treated with trametinib (30 nM)+osimertinib. (D) Timecourse of phospho-MEK1/2 and phospho-ERK1/2 inhibition in PC-9 GR cells treated with DMSO, osimertinib, osimertinib+PAC-1 or osimertinib+trametinib for 6, 24, or 48 hours. See also FIG. 9.
Figure 3:
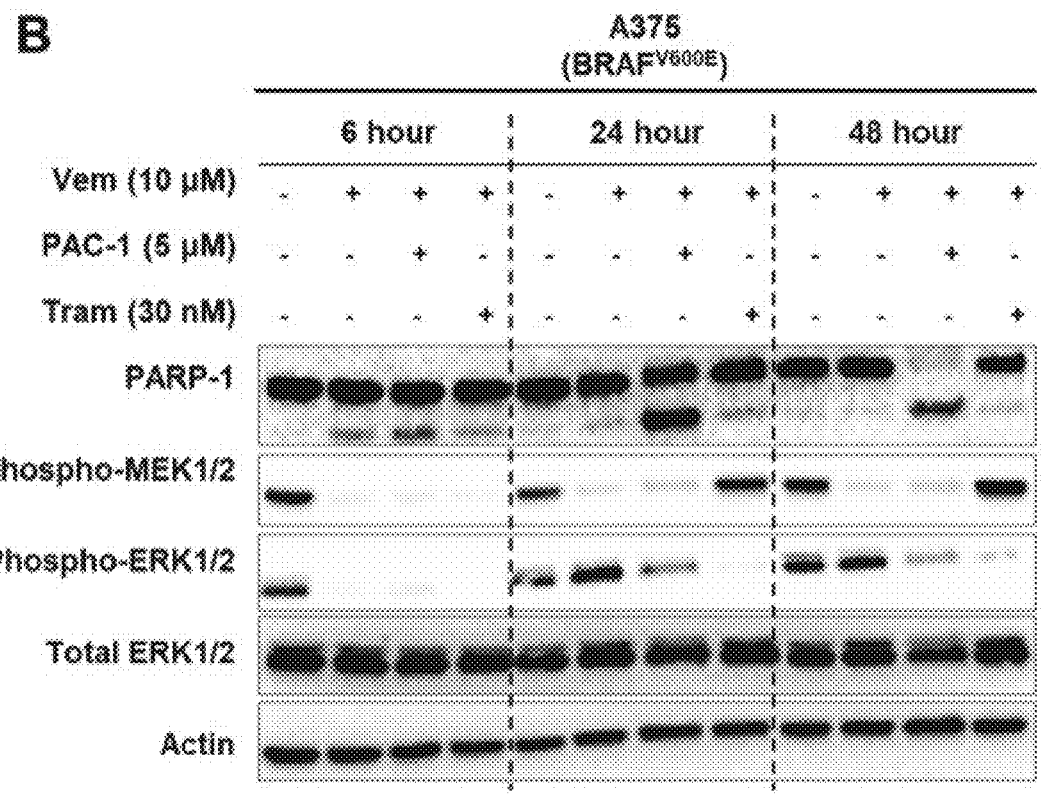
Figure 3:
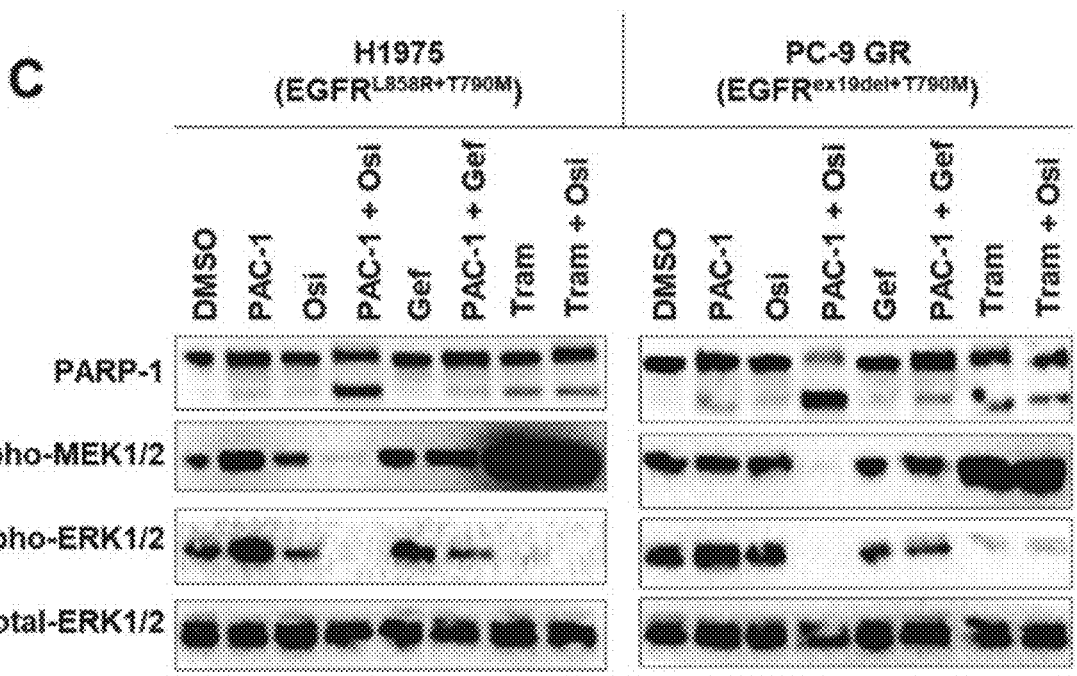
Figure 3:
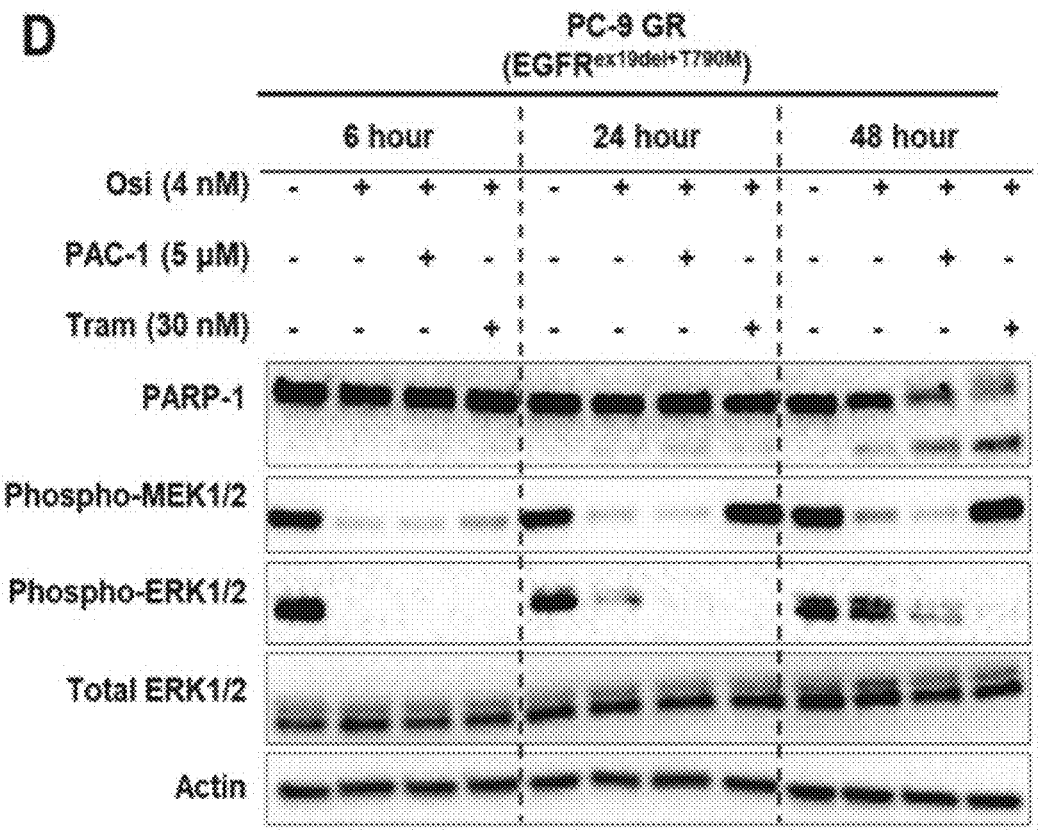

The disclosed results show that co-treatment of a procaspase-3 activator, PAC-1, with diverse targeted kinase inhibitors at clinically relevant concentrations (see Table 2 for predicted effects of each kinase inhibitor on MEK1/2 phosphorylation and caspase activity) is broadly effective in enhancing caspase-3 activity and apoptotic cell death across diverse tumor histologies and driver mutations. The resultant caspase-3 activity leads to enzymatic degradation of both MEK1 and MEK2 kinases and sustained inhibition of both MEK1/2 and ERK1/2 phosphorylation. While sustained ERK1/2 inhibition can be achieved with MEK1/2 inhibitors, this disrupts the negative feedback on RAF kinases, leading to the paradoxical hyper-phosphorylation of MEK1/2. Trametinib was developed as a "feedback buster" to minimize MEK1/2 hyper-phosphorylation but the inhibitory effect is relatively transient as previously shown and consistent with the disclosed results (FIG. 3). In contrast, this disclosure show that caspase-3 mediated degradation of MEK1 and MEK2 kinases is an excellent strategy to inactivate ERK1/2, without the corresponding rebound in MEK1/2 phosphorylation. The disclosed results are supported by the abolishment of ERK1/2 phosphorylation observed upon genomic knockdown of both MEK1 and MEK2. Due to the critical role of MEK1/2 kinases in regulating the MAPK pathway, its sustained inhibition can be advantageous in significantly delaying the onset of acquired resistance.

In contrast to direct procaspase-3 activation using PAC-1, non-specific induction of apoptosis using general cytotoxins such as doxorubicin can lead to hyper-activation of ERK1/2 due to the cellular stress induced by these agents. This observation underscores the importance of using a direct procaspase-3 activator instead of general cytotoxins, in combination with targeted kinase inhibitors, to avoid the paradoxical reactivation of ERK1/2 phosphorylation.

The disclosed results also show that addition of 1-2 µM of PAC-1 (a concentration easily achieved in human patients) is effective in delaying acquired resistance to vemurafenib, osimertinib, and ceritinib in $BRAF^{V600E}$ melanoma, $EGFR^{T790M}$, and EML4-ALK NSCLCs respectively. Moreover, there is a marked benefit of combining PAC-1 with targeted kinase inhibitors as compared to MEK1/2 inhibition (with trametinib) in combination with targeted kinase inhibitors, in dramatically delaying or eliminating resistance. Two mechanisms are likely in play to account for this observation. First, enhanced apoptosis observed in cells treated with PAC-1 combination therapies likely impedes the emergence of resistant clones, as the vast majority of cancer cells are killed. Second, sustained MEK1/2 and ERK1/2 inhibition severely compromise the cells ability to proliferate and form resistant colonies.

Targeted kinase inhibitors have had a dramatic impact on cancer treatment, but resistance has seriously limited the durability of this effect. Instead of developing new drugs for each resistance mechanism, in the work disclosed herein a potentially generalizable strategy has been identified to eliminate or substantially delay the resistance to targeted anticancer therapies, and have successfully demonstrated its efficacy in cancers driven by $BRAF^{V600E}$, $EGFR^{T790M}$, and EML4-ALK kinases. Given that PAC-1 is currently being evaluated in clinical trials (NCT02355535, NCT03332355), and the kinase inhibitors used in this study are already approved by the FDA, the preclinical data results presented herein can inform the design of future trials to investigate PAC-1 combination therapies that may result in delayed or eliminated resistance.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compositions described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods as described herein for treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, lung cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Methods and Materials (Table 1)

Experimental Model and Subject Details

A375, K-562, and SK-MEL-5 were obtained from ATCC. PC-9 GR, H1975, and H3122 were provided by Prof. Eric Haura (Moffitt Cancer Center). PC-9 GR, H1975, and H3122 were cultured in RPMI 1640 supplemented with 10% FBS (Gemini). A375 and SK-MEL-5 were cultured in DMEM+10% FBS. K-562 was cultured in IMDM+10% FBS. All cells were cultured at 37° C. with 5% $CO_2$. Sex of human cell lines: A375 (Female, 54 years old), K-562 (Female, 53 years old), SK-MEL-5 (Female, 24 years old), H3122 (Female, age unknown), H1975 (Female, age unknown), PC-9 GR (Female, age unknown).

TABLE 1

Key resources.

| REAGENT or RESOURCE | SOURCE | IDENTIFIER |
|---|---|---|
| Antibodies | | |
| Beta-Actin HRP | Cell Signaling Technology | Product # 5125 |
| Caspase-3 (Full Length) (Rabbit) | Cell Signaling Technology | Product # 9662 |
| PARP-1 (Rabbit) | Cell Signaling Technology | Product # 9532 |
| MEK1 (Rabbit) | Cell Signaling Technology | Product # 9146 |
| MEK2 (Rabbit) | Cell Signaling Technology | Product # 9147 |
| p-MEK1/2 (Ser217/Ser221) (Rabbit) | Cell Signaling Technology | Product # 9121 |
| p-ERK1/2 (Thr202/Tyr204) (Rabbit) | Cell Signaling Technology | Product # 4370 |
| Total ERK1/2 (Rabbit) | Cell Signaling Technology | Product # 4695 |
| Annexin V-FITC | Southern Biotechnology | Cat # 10040-02 |
| IgG (Rabbit) HRP | Cell Signaling Technology | Product # 7074 |
| Chemicals, Peptides, and Recombinant Proteins | | |
| PAC-1 | Putt, et al., 2006 | N/A |
| Raptinal | Palchaudhuri, et al., 2015 | N/A |
| Vemurafenib | LC Laboratories | Cat # V-2800 |
| Gefitinib | Cayman Chemicals | Cat # 13166 |
| Osimertinib | MedChem Express | Cat # HY-15772 |
| Ceritinib | MedChem Express | Cat # HY-15656 |
| Imatinib | MedChem Express | Cat # HY-15463 |
| Trametinib | MedChem Express | Cat # HY-10999 |
| BSA | Research Products International Corp. | Cat # A30075-100.0 |
| Sulforhodamine B (SRB) | Sigma Aldrich | Cat # 230162 |
| Acetic Acid | Fisher Scientific | Cat # A38-212 |
| Propidium Iodide | Sigma Aldrich | Cat # 81845 |
| Ac-DEVD-AFC | Cayman Chemicals | Cat # 14459 |
| HEPES | Fisher Scientific | Cat # BP310-1 |

TABLE 1-continued

Key resources.

| REAGENT or RESOURCE | SOURCE | IDENTIFIER |
|---|---|---|
| Sodium Chloride | Fisher Scientific | Cat # S271-500 |
| DTT | Sigma Aldrich | DTT-RO ROCHE |
| EDTA | Fisher Scientific | Cat # S311-100 |
| Triton-X-100 | Fisher Scientific | Cat # BP151-100 |
| Q-VD-OPh | Cayman Chemical | Cat # 15260 |
| RIPA Buffer | Cold Spring Harbor Protocols | doi:10.1101/pbd.rec10617 |
| Protease Inhibitor Cocktail III EDTA-Free | Calbiochem | Cat # 539134 |
| Phosphatase Inhibitor Cocktail IV | BioVision | Cat # K282-1 |
| SDS (Tris/Glycine) Buffer (10x) | BioRad | Cat # 161-0732 |
| Sucrose | EMD Millipore | Cat # SX1075 |
| Tris Base | Fisher Scientific | Cat # BP 152-500 |
| Calcium Chloride | Fisher Scientific | Cat # AC349610 |
| Critical Commercial Assays | | |
| Pierce BCA Reagents A/B | Thermo Fisher Scientific | Cat # 23225 |
| Experimental Models: Cell Lines | | |
| A375 | ATCC | Cat # CRL-1619 |
| K-562 | ATCC | Cat # CCL-243 |
| PC-9 GR | Prof. Eric Haura, Moffitt Cancer Center | N/A |
| H3122 | Prof. Eric Haura, Moffitt Cancer Center | N/A |
| H1975 | Prof. Eric Haura, Moffitt Cancer Center | N/A |
| SK-MEL-5 | ATCC | Cat # HTB-70 |
| Software and Algorithms | | |
| ANOVA 2 Way T Test | OriginPro V10 | https://www.originlab.com/ |
| FCS Express V5 | De Novo software | https://www.denovosoftware.com/ |
| Two Way T-Test | Microsoft Excel 16.12 | https://products.office.com/en-us/home |
| Other | | |
| Mini-PROTEAN TGX Gels (4-20%) | BioRad | Cat # 456-1096 |
| PDVF Membrane | Millipore | Cat # IPVH00010 |
| Stripping Buffer | Thermo Fisher | Cat # 21059 |
| SuperSignal West Pico | Thermo Fisher | Cat # 34577 |
| BD LSR II Flow Cytometer | BD Biosciences | n/a |
| GelDoc XR | BioRad | Cat # 1708195 |
| ChemiDoc Touch | BioRad | Cat # 17001401 |
| SpectraMax M3 | Molecular Devices | Cat # M3 |

Cell Line Authentication

All human cell lines used in this study (PC-9 GR, H1975, SK-MEL-5, A375, K-562, and H3122) have been authenticated using the PowerPlex16HS Assay (Promega) as described previously (Peh, et al., Mol. Cancer Ther., 2016, 15, 1859): 15 Autosomal Loci, X/Y at the University of Arizona Genetics Core (UAGC). >1 million cells were harvested and lysed using the cell lysis buffer (50 mM Tris, 50 mM EDTA, 25 mM sucrose, 100 mM NaCl, 1% SDS, pH 8). DNA extraction and short tandem repeats (STRs) profiling for each cell line were carried out at the UAGC. The resulting autosomal STR profiles were compared to reference databases such as ATCC, DSMZ, and JCRB.

Cell Viability Assay 1000 cells were seeded per well in a 96-well plate and allowed to adhere before DMSO solutions of osimertinib, gefitinib, or PAC-1 were added to each well. Final concentration of DMSO in each well is 0.5%. At the end of 5 days, viability was assessed by the sulforhodamine B (SRB) assay sulforhodamine B (SRB) assay. Briefly, 100 µL of 10% trichloroacetic acid (TCA) was added in each well and the plate was incubated for at least 1 hour at 4° C. After the 4° C. incubation, the plate was washed with water and allowed to dry for at least 1 hour at room temperature. 100 µL of SRB dye (1% w/v) was added to each well and incubated for 30 minutes at room temperature. At the end of the 30 minutes incubation, the plate was washed with 1% acetic acid solution and allowed to dry at room temperature. Finally, 200 µL of Tris solution (pH>10) was added to each well to dissolve the SRB dye. The absorbance of each well was read with a SpectraMax M3 plate reader (Molecular Devices) at 510 nm.

Caspase-3/-7 Activity Assay

For the EGFR$^{T790M}$ cell lines, 4,000 cells were seeded in each well of 96-well plates and allowed to adhere overnight. The next day, indicated concentrations of PAC-1 or osimertinib, were added and treated for 0, 2, 4, 24, 30, 35, 44 and 48 hour. K-562 cells were seeded at 3,000 cells per well and treated with indicated concentrations of PAC-1 or imatinib for 0, 2, 4, 24, 48, 68, and 72 hour. H3122 cells were seeded at 4,000 cells per well and allowed to adhere overnight. The cells were then treated with indicated concentrations of PAC-1 or ceritinib for 0, 2, 4, 24, 44, and 48 hour. 10 µM raptinal was used as the positive control throughout the experiment. After indicated incubation times, the cells were lysed and caspase-3/-7 activity was assessed via addition of bifunctional lysis and activity buffer (200 mM HEPES, 400 mM NaCl, 40 mM DTT, 0.4 mM EDTA, 1% Triton-X, pH 7.4) with 50 µM of fluorogenic Ac-DEVD-AFC substrate ($\lambda_{ex}$=405 nm, $\lambda_{em}$=505 nm). Plates were pre-incubated at 37° C. for 30 minutes in the SpectraMax M3 (Molecular Devices) plate reader and then read for 30 minutes at 3-minute intervals. Slopes for each well were calculated and averaged over six technical replicates. Activity is normalized to the maximal and minimal activity observed within the assay.

Immunoblotting

Cells were lysed using RIPA buffer containing phosphatase (BioVision) and protease inhibitor cocktail (Calbiochem). Protein concentration was determined using the BCA assay (Pierce). Cell lysates containing 8-20 µg of protein were loaded into each lane of 4-20% gradient gels (BioRad) and ran for SDS-PAGE. Proteins were transferred onto PDVF membrane (Millipore) for Western blot analysis. Blots were blocked with BSA for one hour followed by incubation with primary antibody overnight (manufacturer's recommended dilutions). Secondary antibody was incubated for one hour. Blots were then imaged with a ChemiDoc Touch after incubation with SuperSignal West Pico Solution following manufacturer's protocols.

Assessment of Apoptosis by Flow Cytometry

For the EGFR$^{T790M}$ cell lines, 40,000 cells were seeded in 12-well plates and allowed to adhere overnight. The next day, indicated concentrations of PAC-1 or osimertinib were added and allowed to incubate at 37° C. for 48 hours. K-562 cells were seeded at 30,000 and incubated with PAC-1 or imatinib for 72 hours. In 12-well plates, 40,000 H3122 cells were seeded and allowed to adhere overnight. The next day, they were incubated with PAC-1 or ceritinib for 48 hours. After the indicated incubation period, cells were harvested and resuspended in 450 µL of cold buffer (10 mM HEPES, 140 mM NaCl, 2.5 mM CaCl$_2$, pH 7.4) premixed with Annexin V-FITC and PI dyes. Samples were analyzed on a BD Biosciences LSRII flow cytometer, and data analysis was performed using FSC Express Version5.

Q-VD-OPh Protection by Flow Cytometry

A375 (BRAF$^{V600E}$) cells were seeded with 70,000 cells/well in 12-well plates and allowed to adhere overnight. The next day, indicated concentrations of PAC-1, vemurafenib, trametinib, and/or Q-VD-OPh were added and cells were incubated at 37° C. for 48 hours. For the EGFR$^{T790M}$ cell line, PC-9 GR, 40,000 cells were seeded in 12-well plates and allowed to adhere overnight. The next day, indicated concentrations of PAC-1, osimertinib, and Q-VD-OPh were added and allowed to incubate at 37° C. for 48 hours. In 12-well plates, 40,000 H3122 cells were seeded and allowed to adhere overnight. The next day, they were incubated with PAC-1, ceritinib, and/or Q-VD-OPh for 48 hours. K-562 cells were seeded with 35,000 cells/well in 12-well plates. The next day, indicated concentrations of PAC-1, imatinib, and/or Q-VD-OPh were added and cells were incubated at 37° C. for 48 hours. After the indicated incubation period, cells were harvested and resuspended in 450 µL of cold buffer (10 mM HEPES, 140 mM NaCl, 2.5 mM CaCl$_2$, pH 7.4) premixed with Annexin V-FITC and PI dyes. Samples were analyzed on a BD Biosciences LSRII flow cytometer, and data analysis was performed using FSC Express Version5.

Long Term Experiments in BRAF$^{V600E}$ Cell Lines

This assay was performed as described previously. Briefly, 100-250 cells were seeded and allowed to adhere overnight. The next day, cells were treated with indicated concentrations of PAC-1, vemurafenib or trametinib for 10, 20, 25 or 30 days. Media was refreshed with new compounds added every 3-4 days. At the end of the incubation period, cells were fixed 10% trichloroacetic acid, stained with SRB, imaged using GelDoc XR (BioRad), and absorbance at 510 nm read using SpectraMax M3 (Molecular Devices) plate reader.

Long Term Experiments with EGFR$^{T790M}$ Cell Lines

In 12 well plates, PC-9 GR or H1975 cells were seeded at 2,000 cells per well and allowed to adhere overnight. The next day, cells were treated with indicated concentrations of PAC-1 or osimertinib for 8 or 28 days. Media was refreshed every 3-4 days with new compounds. For experiments comparing the effect of PAC-1 combination versus trametinib combination, PC-9 GR cells were seeded at 10,000 cells per well in 6 well plates and allowed to adhere overnight. The next day, cells were treated with indicated concentrations of PAC-1, osimertinib, or 5 nM trametinib for 8, 28, or 35 days. Media was refreshed every 3-4 days with new compounds. At the end of the incubation period, cells were fixed 10% trichloroacetic acid, stained with SRB, imaged using GelDoc XR, and absorbance at 510 nm read using SpectraMax M3 (Molecular Devices) plate reader.

Long Term Experiments with EML4-ALK Cell Line

H3122 cells were seeded at 10,000 cells per well in 6 well plates and allowed to adhere overnight. The next day, cells were treated with indicated concentrations of PAC-1, osimertinib, or 5 nM trametinib for 8, 20, or 32 days. Media was refreshed every 3-4 days. At the end of the incubation period, cells were fixed 10% trichloroacetic acid, stained with SRB, imaged using GelDoc XR, and absorbance at 510 nm read using SpectraMax M3 (Molecular Devices) plate reader.

TABLE 2

Analysis of kinases that phosphorylate caspases and the predicted effects of indicated kinase inhibitors on these caspase kinases as well as MEK1/2 phosphorylation. Related to FIGS. 1 and 2.

| Caspase phosphorylated | Kinase | Outcomes of phosphorylation | % Inhibition at indicated concentrations or IC$_{50}$ values | | | |
|---|---|---|---|---|---|---|
| | | | Vemurafenib (Nature, 2010 467, 596-599) | Osimertinib (Cancer Discov. 2014, 4, 1046-1061) | Ceritinib (J. Med. Chem. 2013, 56, 5675-5690) | Imatinib (Genes Cells 2013, 18, 110-122) |
| | MEK1 (MAP2K1) | | <10% at 1 µM | Not reported | Not reported | 18% at 1 µM |
| | MEK2 (MAP2K2) | | <10% at 1 µM | Not reported | Not reported | 5.9% at 1 µM |
| Caspase-2 | DNA-PK | Activation | Not reported | Not reported | Not reported | Not reported |
| Caspase-2 | CaMKII | Suppression | <10% at 1 µM | Not reported | Not reported | Not observed |

TABLE 2-continued

Analysis of kinases that phosphorylate caspases and the predicted effects of indicated kinase inhibitors on these caspase kinases as well as MEK1/2 phosphorylation. Related to FIGS. 1 and 2.

| | | | % Inhibition at indicated concentrations or $IC_{50}$ values | | | |
|---|---|---|---|---|---|---|
| Caspase phosphorylated | Kinase | Outcomes of phosphorylation | Vemurafenib (*Nature*, 2010 467, 596-599) | Osimertinib (*Cancer Discov.* 2014, 4, 1046-1061) | Ceritinib (*J. Med. Chem.* 2013, 56, 5675-5690) | Imatinib (*Genes Cells* 2013, 18, 110-122) |
| Caspase-2 | PP1 | Suppression | Not observed | Not reported | Not reported | Not reported |
| Caspase-2 | CK2 | Suppression | Not observed | Not reported | Not reported | Not observed |
| Caspase-3 | PKCδ | Enhancement | <20% at 1 μM | Not reported | Not reported | Not observed |
| Caspase-3 | p38 MAPK (MAPK11) | Suppression | <10% at 1 μM | Not reported | Not reported | Not observed |
| Caspase-3 | PP2A | Suppression | Not observed | Not reported | Not reported | Not reported |
| Capsase-8 | ND | SHP1 binding | Not observed | Not reported | Not reported | Not reported |
| Capsase-8 | Src | Suppression | 2.4 μM $IC_{50}$ | Not reported | 1694 nM $IC_{50}$ | 5.3% at 1 μM |
| Capsase-8 | Fyn | Suppression | <20% at 1 μM | Not reported | Not reported | 29.6% at 1 μM |
| Capsase-8 | SHP1 | Suppression | Not observed | Not reported | Not reported | Not reported |
| Capsase-8 | Lyn | Suppression | Not observed | Not reported | 840 nM $IC_{50}$ (in vitro), 2306 nM $IC_{50}$ (Ba/F3 cells) | 190 nM $IC_{50}$ |
| Capsase-8 | SHP1 | Suppression | Not observed | Not reported | Not reported | Not reported |
| Caspase-8 | p38 MAPK (MAPK11) | Suppression | <10% at 1 μM | Not reported | Not reported | Not observed |
| Caspase-9 | ERK1/2 (MAPK1) | Suppression | <10% at 1 μM | Not reported | Not reported | Not observed |
| Caspase-9 | CDK1 | Suppression | <10% at 1 μM | Not reported | Not reported | 1.8% at 1 μM |
| Caspase-9 | DYRK1A | Suppression | <10% at 1 μM | Not reported | Not reported | 2.2% at 1 μM |
| Caspase-9 | p38 MAPK (MAPK11) | Suppression | <10% at 1 μM | Not reported | Not reported | Not observed |
| Caspase-9 | PP1α | Suppression | Not observed | Not reported | Not reported | Not reported |
| Caspase-9 | PKCζ | Suppression | <20% at 1 μM | Not reported | Not reported | Not observed |
| Caspase-9 | c-Abl | Enhancement | <10% at 1 μM | Not reported | Not reported | 190 nM $IC_{50}$ |
| Caspase-9 | PKA | No effect | Not observed | Not reported | Not reported | Not observed |
| Caspase-9 | AKT | Suppression | Not observed | Not reported | >10 μM | 3.2% at 1 μM |
| Caspase-9 | CK2 | Protection from caspase-8 cleavage | Not observed | Not reported | Not reported | Not observed |

Quantification and Statistical Analysis

Data are presented as mean values±standard error of the mean (s.e.m.). Levels of significance were determined by two-way t-test for control versus experimental groups using Microsoft Excel. To determine if the increase in caspase-3 activity was synergistic, two-way ANOVA analysis was performed for DMSO-, single-agent-versus combination-treated samples using OriginPro (Version 10, Origin Lab). No analyses were performed to determine whether the data met the assumptions of this statistical approach. Statistical values, including the number of independent replicates and statistical significance, are reported in the Figure Legends.

Example 2. Pharmaceutical Dosage Forms

The following formulations illustrate representative pharmaceutical dosage forms that may be used for the therapeutic or prophylactic administration of the combination compounds described herein, (e.g., PAC-1 and a second active agent), or pharmaceutically acceptable salts or solvates thereof (hereinafter referred to as 'Composition X', which can be one active agent or a combination of two active agents):

| (i) Tablet 1 | mg/tablet |
|---|---|
| 'Composition X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Composition X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Composition X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Composition X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Composition X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Composition X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Composition X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Composition X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Composition X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Composition X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Composition X' | 5% |
| Stearic acid | 10% |
| Glyceryl monostearate | 3% |
| Polyoxyethylene stearyl ether | 3% |
| Sorbitol | 5% |
| Isopropyl palmitate | 2% |

-continued

| (xi) Topical Cream 2 | wt. % |
|---|---|
| Methyl Paraben | 0.2% |
| Purified water | q.s. to 100 g |

Example 3. Tablet Forms

The following formulation illustrates representative pharmaceutical dosage forms that may be used for the therapeutic or prophylactic administration of the combination compounds described herein (e.g., PAC-1 and the second active agent), or pharmaceutically acceptable salts or solvates thereof:

| (i) Tablet A | mg/tablet |
|---|---|
| PAC-1 | 250.0 |
| Microcrystalline cellulose | 127.5 |
| Mannitol | 50.0 |
| Sodium starch glycolate | 50.0 |
| Fumed silica | 2.5 |
| Hydroxypropyl cellulose | 15.0 |
| Sodium stearyl fumarate | 5.0 |
| | 500.0 |

| (ii) Tablet B | mg/tablet |
|---|---|
| Second agent | 250.0 |
| Microcrystalline cellulose | 127.5 |
| Mannitol | 50.0 |
| Sodium starch glycolate | 50.0 |
| Fumed silica | 2.5 |
| Hydroxypropyl cellulose | 15.0 |
| Sodium stearyl fumarate | 5.0 |
| | 500.0 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method of inhibiting the growth or proliferation of cancer cells comprising contacting cancer cells with an effective amount of a composition comprising:
   (a) the compound PAC-1:

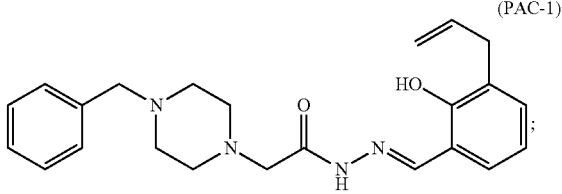 [SMILES: C=CCc1cccc(/C=N/NC(=O)CN2CCN(Cc3ccccc3)CC2)c1O]

(b) at least one second active agent, wherein the second active agent is an inhibitor of a mutant kinase or an inhibitor of a fusion kinase; and
   c) optionally a pharmaceutically acceptable diluent, excipient, carrier, or a combination thereof;
   wherein:
   i) the concentration of PAC-1 is about 5 µM, the second active agent is osimertinib, and the concentration of osimertinib is about 1 nM to about 4 nM; or
   ii) the concentration of PAC-1 is about 2.5 µM to about 5 µM, the second active agent is ceritinib, and the concentration of ceritinib is about 5 nM to about 30 nM; or
   iii) the concentration of PAC-1 is about 5 µM to about 7.5 µM, the second active agent is imatinib, and the concentration of imatinib is about 60 nM to about 100 nM;
   thereby inhibiting the growth or proliferation of the cancer cells.

2. A method of inducing apoptosis in a cancer cell comprising contacting the cancer cell with an effective amount of a composition comprising:
   (a) the compound PAC-1:

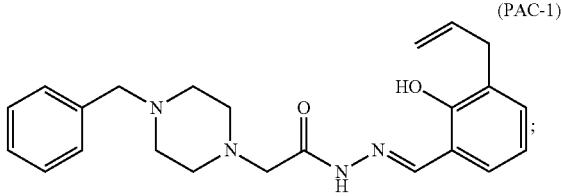 [SMILES: C=CCc1cccc(/C=N/NC(=O)CN2CCN(Cc3ccccc3)CC2)c1O]

(b) at least one second active agent, wherein the second active agent is an inhibitor of a mutant kinase or an inhibitor of a fusion kinase; and
   c) optionally a pharmaceutically acceptable diluent, excipient, carrier, or a combination thereof;
   wherein:
   i) the concentration of PAC-1 is about 5 µM, the second active agent is osimertinib, and the concentration of osimertinib is about 1 nM to about 4 nM; or
   ii) the concentration of PAC-1 is about 2.5 µM to about 5 µM, the second active agent is ceritinib, and the concentration of ceritinib is about 5 nM to about 30 nM; or
   iii) the concentration of PAC-1 is about 5 µM to about 7.5 µM, the second active agent is imatinib, and the concentration of imatinib is about 60 nM to about 100 nM;
   wherein apoptosis is thereby induced in the cancer cell.

3. A method of treating a cancer comprising administering to a patient in need thereof, concurrently or sequentially, a combination of a therapeutically effective amount of the compound PAC-1:

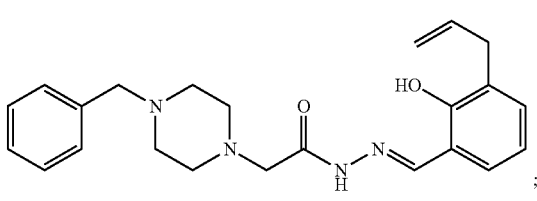

and an effective amount of a second active agent, wherein the second active agent is an inhibitor of a mutant kinase or an inhibitor of a fusion kinase;
   wherein:
   i) the concentration of PAC-1 is about 5 µM, the second active agent is osimertinib, and the concentration of osimertinib is about 1 nM to about 4 nM; or
   ii) the concentration of PAC-1 is about 2.5 µM to about 5 µM, the second active agent is ceritinib, and the concentration of ceritinib is about 5 nM to about 30 nM; or
   iii) the concentration of PAC-1 is about 5 µM to about 7.5 µM, the second active agent is imatinib, and the concentration of imatinib is about 60 nM to about 100 nM;
   wherein the cancer is lung cancer or leukemia, and the cancer is thereby treated.

4. The method of claim 3 wherein a cancer is treated by degrading or abolishing both MEK-1 and MEK-2 kinases, thereby effectively inhibiting the MAPK signaling pathway and inducing apoptosis in a cancer cell, by inhibiting phosphorylation of MEK-1 and MEK-2, ERK-1 and ERK-2, or a combination thereof; or
   a pro-apoptotic Bcl-2 protein (BIM) is upregulated.

5. The method of claim 3 wherein the cancer is a metastatic form.

6. The method of claim 3 wherein resistance to treatment of the cancer in a patient in need thereof is reduced, delayed, or eliminated.

7. The method of claim 3 wherein the compound PAC-1 and the second active agent are concurrently administered to a cancer patient.

8. The method of claim 3 wherein the compound PAC-1 and the second active agent are sequentially administered to a cancer patient.

9. The method of claim 3 further comprising administering to the patient, concurrently or sequentially, a therapeutically effective amount of a V600E mutated BRAF kinase inhibitor, or a combination thereof.

10. The method of claim 3 further comprising administering to the patient, concurrently or sequentially, a therapeutically effective amount of a MEK inhibitor wherein the MEK inhibitor is trametinib, cobimetinib, binimetinib, or a combination thereof.

11. The method of claim 9 wherein the mutated BRAF kinase inhibitor is vemurafenib, dabrafenib, encorafenib, or a combination thereof.

12. The method of claim 1 wherein the cancer cells are lung cancer cells or leukemia cells.

13. The method of claim 1 wherein the composition comprises a) a carrier comprising water, buffer, a sugar, cellulose, cyclodextrin, dimethyl sulfoxide, polyethylene glycol, tocopherol, a liposome, a micelle, or a combination thereof, or b) an excipient comprising a binder, a lubricant, a sorbent, a vehicle, a disintegrant, a preservative, or a combination thereof.

14. The method of claim 2 wherein the cancer cell is a lung cancer cell or leukemia cell.

15. The method of claim 3 wherein the cancer is lung cancer.

16. The method of claim 3 wherein the cancer is leukemia.

17. The method of claim 3 wherein the second agent is osimertinib, the concentration of PAC-1 is about 5 µM, the concentration of osimertinib is about 1 nM to about 4 nM, and the cancer is lung cancer.

18. The method of claim 3 wherein the second agent is ceritinib, the concentration of PAC-1 is about 2.5 µM to about 5 µM, the concentration of ceritinib is about 5 nM to about 30 nM, and the cancer is lung cancer.

19. The method of claim 3 wherein the second agent is imatinib, concentration of PAC-1 is about 5 µM to about 7.5 µM, the concentration of imatinib is about 60 nM to about 100 nM, and the cancer is leukemia.

* * * * *